US011774441B2

(12) United States Patent
Brandenstein et al.

(10) Patent No.: US 11,774,441 B2
(45) Date of Patent: Oct. 3, 2023

(54) METHOD FOR DETERMINING THE FERTILITY OF SPERMATOZOA COMPRISING DETECTION OF VIMENTIN VARIANT 3

(71) Applicant: Universität zu Köln, Cologne (DE)

(72) Inventors: Melanie von Brandenstein, Lindlar (DE); Ali Tok, Hürth (DE)

(73) Assignee: Universität zu Köln, Cologne (DE)

( * ) Notice: Subject to any disclaimer, the term of this patent is extended or adjusted under 35 U.S.C. 154(b) by 0 days.

(21) Appl. No.: 16/603,118

(22) PCT Filed: Apr. 6, 2018

(86) PCT No.: PCT/EP2018/058923
§ 371 (c)(1),
(2) Date: Oct. 4, 2019

(87) PCT Pub. No.: WO2018/185322
PCT Pub. Date: Oct. 11, 2018

(65) Prior Publication Data
US 2020/0110076 A1 Apr. 9, 2020

(30) Foreign Application Priority Data
Apr. 6, 2017 (EP) .................................... 17165191

(51) Int. Cl.
*G01N 33/50* (2006.01)
*C07K 16/18* (2006.01)
*G01N 33/563* (2006.01)

(52) U.S. Cl.
CPC ......... *G01N 33/5091* (2013.01); *C07K 16/18* (2013.01); *G01N 33/563* (2013.01); *G01N 2800/367* (2013.01)

(58) Field of Classification Search
None
See application file for complete search history.

(56) References Cited

FOREIGN PATENT DOCUMENTS

| WO | 9740386 A1 | 10/1997 |
| WO | 2005/121803 A1 | 12/2005 |
| WO | 2014/154686 A1 | 10/2014 |

OTHER PUBLICATIONS

Funke et al., Disease Markers, 2019; https://doi.org/10.1155/2019/9803498; 5 pages total. (Year: 2019).*
The Mayo Clinic website available at https://www.mayoclinic.org/diseases-conditions/male-infertility/diagnosis-treatment/drc-20374780?p=1; downloaded Nov. 1, 2021 (Year: 2021).*
Gloria et al., Journal of Animal Science and Biotechnology (2016) 7:30 (Year: 2016).*
The World Health Organization, ICD-10-Mortality 2e-vol. 1—2016; p. 829 (Year: 2016).*
The World Health Organization, ICD-10-Mortality 2e-vol. 1—2016; p. 1062 (Year: 2016).*
Genbank, "Vimentin [Bos taurus]", Genbank Accession No. NP_776394.2, Jun. 23, 2018, 7 pages.
Genbank, "Vimentin [Cavia porcellus]", Genbank Accession No. NP_001166511.1, Jan. 29, 2018, 1 page.
Genbank, "Vimentin [Equus caballus]", Genbank Accession No. NP_001230074.1, Jun. 16, 2018, 2 pages.
Genbank, "Vimentin [Gallus gallus]", Genbank Accession No. NP_001041541.1, Jan. 16, 2016, 3 pages.
Genbank, "Vimentin [Mus musculus]", Genbank Accession No. CAA39807.1, Apr. 18, 2005, 2 pages.
Genbank, "Vimentin [Mus Musculus]", Accession No. NP_035831.2, Dec. 10, 2019, 7 pages.
Genbank, "Vimentin [Oncorhynchus mykiss]", Genbank Accession No. CAA90601.1, Jun. 27, 2018, 2 pages.
Genbank, "Vimentin [Pan troglodytes]", Genbank Accession No. NP_001009148.1, Jun. 23, 2018, 7 pages.
Genbank, "Vimentin [Rattus norvegicus]", Gen Bank Accession No. NP_112402.1, Jun. 23, 2018, 8 pages.
Genbank, "Vimentin [Salmo salar]", Genbank Accession No. NP_001133947.1,, Apr. 24, 2016, 2 pages.
Genbank, "Vimentin Variant 3 [*Homo sapiens*]", Genbank Accession No. ACA06103.1, Feb. 20, 2008, 1 page.
Genbank, "vimentin, partial [Mesocricetus auratus]", Genbank Accession No. AAA37104.1,, Aug. 1, 2016, 1 page.
Markova et al. "Asymmetric Vimentin Distribution in Human Spermatazoa" (2002) Folia Biol (Praha) 48:160-162.
Alam et al. "Di(n-butyl) Phthalate Induces Vimentin Filaments Disruption in Rat Sertoli Cells: A Possible relation with Spermatogenic Cell Apoprosis" (2010) Anat Histol Embryol 39(3):186-193.
Marinova et al. "Distribution of vimentin in abnormal human spermatazoa" (1996) Andrologia 28(5):287-289.
Von Brandenstein et al. "Vimentin 3, the New Hope, Differentiating RCC versus Oncocytoma" (2015) Disease Markers, Article ID 368534. doi:10.1155/2015/368534.
Thakkar et al. "Proteomic Studies Coupled with RNAi Methodologies can Shed Further Lighten the Downstream Effects of Telomerase in Glioma" (2011) Cancer Invest 29:113-122.
http://www.ncbi.nlm.nih.gov/protein/167887751 amino acid sequence of human Vim3.

(Continued)

*Primary Examiner* — Christina M Borgeest
(74) *Attorney, Agent, or Firm* — RAPHAEL BELLUM PLLC

(57) ABSTRACT

The present invention relates to a method for determining the fertility of spermatozoa, said method comprising determining the total content of Vimentin variant 3 (Vim3) per spermatozoon and/or the spatial localization of the Vim3 in the spermatozoa, wherein a decreased amount of total content and/or decreased amount of (or even missing) accumulation of Vim3 in the mid piece of the spermatozoa indicates decreased fertility. Further, the present invention refers to a dipstick usable for this method. Moreover, the present invention relates to further methods and uses in the context of the present invention.

25 Claims, 7 Drawing Sheets

Specification includes a Sequence Listing.

(56) References Cited

OTHER PUBLICATIONS

Preechakasedkit. "Development of a one-step immunochromatographic strip test using gold nanoparticles for the rapid detection of *Salmonella typhi* in human serum" (2012) Biosens Bioelectron 31(1):562-566.

Tao et al. "A rapid one-step immunochromatographic test strip for rabies detection using canine serum samples" (2014) Lett Appl Microbiol 59(2):247-251.

Wang et al. "A rapid immunochromatographic test strip for detecting rabies virus antibody" (2010) J Virol Methods 170(1-2):80-85.

* cited by examiner

SEQUENCE LISTING

<160> NUMBER OF SEQ ID NOS: 2

<210> SEQ ID NO 1
<211> LENGTH: 431
<212> TYPE: PRT
<213> ORGANISM: Homo sapiens

<400> SEQUENCE: 1

```
Met Ser Thr Arg Ser Val Ser Ser Ser Tyr Arg Arg Met Phe Gly
1               5                   10                  15

Gly Pro Gly Thr Ala Ser Arg Pro Ser Ser Arg Ser Tyr Val Thr
            20                  25                  30

Thr Ser Thr Arg Thr Tyr Ser Leu Gly Ser Ala Leu Arg Pro Ser Thr
            35                  40                  45

Ser Arg Ser Leu Tyr Ala Ser Ser Pro Gly Gly Val Tyr Ala Thr Arg
50                      55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
                100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
130                 135                 140

Arg Leu Gly Asp Leu Tyr Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
            195                 200                 205

Asp Val Asp Asn Ala Ser Leu Ala Arg Leu Asp Leu Glu Arg Lys Val
        210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
    275                 280                 285

Glu Trp Tyr Lys Ser Lys Phe Ala Asp Leu Ser Glu Ala Ala Asn Arg
290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
            355                 360                 365

Ile Gln Asn Met Lys Glu Glu Met Ala Arg His Leu Arg Glu Tyr Gln
        370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
```

```
                          405                 410                 415
Asn Phe Ser Ser Leu Asn Leu Arg Gly Lys His Phe Ile Ser Leu
                420                 425                 430

<210> SEQ ID NO 2
<211> LENGTH: 8
<212> TYPE: PRT
<213> ORGANISM: Homo sapiens

<400> SEQUENCE: 2

Arg Gly Lys His Phe Ile Ser Leu
1               5
```

METHOD FOR DETERMINING THE FERTILITY OF SPERMATOZOA COMPRISING DETECTION OF VIMENTIN VARIANT 3

CROSS-REFERENCES TO RELATED APPLICATIONS

This application is a national stage application filed under 35 U.S.C. § 371, of International Patent Application No. PCT/EP2018/058923, filed Apr. 6, 2018, which claims the benefit of and priority under 35 U.S.C. § 119(e) to European Patent Application No. EP17165191.2, filed Apr. 6, 2017, the entire contents of which are hereby expressly incorporated by reference herein.

INCORPORATION BY REFERENCE OF SEQUENCE LISTING

The contents of the text file named "P70409PC-Sequence-Listing. TXT", which was created on Aug. 31, 2017, and is 4,079 bytes in size, are hereby incorporated by reference in their entireties and for all purposes.

The present invention relates to a method for determining the fertility of spermatozoa, said method comprising determining the total content of Vimentin variant 3 (Vim3) per spermatozoon and/or the spatial localization of the Vim3 in the spermatozoa, wherein a decreased amount of total content and/or decreased amount of (or even missing) accumulation of Vim3 in the mid piece of the spermatozoa indicates decreased fertility. Further, the present invention refers to a dipstick usable for this method. Moreover, the present invention relates to further methods and uses in the context of the present invention.

Unintended childlessness is a widespread phenomenon in modern societies. Male infertility is a global population health problem and around 48.5 million couples suffer under infertility worldwide. Around 30 million men worldwide are infertile with the highest rates in Africa and Eastern Europe. Investigations have shown that childlessness is often a consequence of insufficient male fertility caused by a decreased level fertility of the spermatozoa. This may be associated with psychological stress for the man.

Several different causes of infertility in men exist, the most common is reason is frequently unknown (40-50%), gonad disorder (30-40%), a disorder in the sperm transport (10-20%) or a hypothalamic or pituitary disorder (1-2%). Sperm can be abnormal for several different reasons; the most common reasons are unusually short life span of the sperm or low mobility, or both in combination. Sperm abnormalities can be caused by different factors like e.g. inflammation of the testis, varicoceles (swollen vains in the scrotum), abnormally developed testis, genetic disorders, hormone problems. When the fertility of the spermatozoa are severely diminished, the insufficient male fertility may be considered as a pathologic condition such as a condition according to any of classes N46 or R86 of the $10^{th}$ revision of the International Statistical Classification of Diseases and Related Health Problems of the World Health Organization (WHO) in the version of 2016 (ICD-10).

According to the nomenclature of the WHO (world health organization), ejaculates can be divided into several different groups:
- (i) normozoospermia: normal ejaculate (volume>2.0 ml, concentration>$20\times10^6$/ml, Motility>50% Morphology>30% with normal morphology)
- (ii) oligozoospermia: sperm concentration fewer than $20\times10^6$/ml;
- (iii) asthenozoospermia: fewer than 50% spermatozoa with forward progression or fewer than 25% spermatozoa with no movement;
- (iv) teratozoospermia: fewer than 30% spermatozoa with normal morphology;
- (v) oligo-astheno-teratozoospermia (OAT syndrome): signifies disturbance of all three variables; and
- (vi) azoospermia: no spermatozoa in the ejaculate.

Male infertility usually occurs because of sperms with abnormal shape, the sperm quality is not high enough or a problem with the ejaculation. Exemplarily such pathological condition may be oligozoospermia, asthenozoospermia, teratozoospermia or a combination of more than one of these conditions. Spermatozoa of particularly low fertility may be obtained from individuals suffering from oligo-astheno-teratozoospermia (OAT syndrome).

It will be understood that a decreased level fertility of the spermatozoa plays a significant role when considering means for considering further therapeutic or non-medicinal steps. Exemplarily, unintendedly childless couples are often interested to know whether the infertility is caused by the male and/or female body in order to consider suitable treatments or sperm or egg donation.

Accordingly, one of the factors of particular interest for considering further steps is the determination of the fertility of spermatozoa. Likewise, the determination of the fertility of spermatozoa is also of interest for sperm banks in order to sort sperm donations of low fertility out.

In addition, an assessment of the fertility of spermatozoa also plays a significant role when breeding animals. Today, the vast majority of larger sized farm animals such as bovines is bred by means of artificial insemination of the female animals. In this context, numerous aliquots of sperm donations are provided to the farmers. Farmers are on the one hand interested in good breeding success and on the other hand in well-fertile progeny. Likewise, also in projects for conserving biodiversity, an assessment of the fertility of spermatozoa of the animals to be protected is of considerable interest, e.g., when zoos breed endangered species.

Summarized, for humans interested in children as well as for the breeding of non-human animals, an assessment of the fertility of spermatozoa is of considerable interest.

In the art, the fertility of spermatozoa is mostly assessed by means of obtaining a fresh sperm donation and observing concentration and mobility of the spermatozoa comprised therein under a microscope. A lower concentration or mobility is frequently correlated with a lower fertility.

This procedure has severe technical drawbacks. First, a fresh sperm donation not older than few hours is required. Under normal conditions, these samples should even not be older than 15 min since the liquefaction process is also of importance regarding the fertility of man. Ejaculates which were not liquefied after 60 min were too viscous and the patient suffers under a so called hyperviscosity and can be responsible for infertility. Though this hyperviscosity imbalance is treatable with α-chymotrypsin, this temporal restrictions put inopportune pressure on the sperm donor as well as the investigator. The procedure is rather complicate to be handled. Second, in order to avoid falsification of the results due to lower spermatozoa concentrations, the donor has to stick to a preceding abstinence time. Third, the mere observance of the concentration and mobility of spermatozoa may lead to false positive as well as false negative results. Further, for this special ejaculate examination it is necessary that the patients is sexual inactive for at least 3 to 5 days.

In the view of the above, additional and alternative methods are desired to enable the assessment of the fertility of spermatozoa in an easier way based on a clearer readout.

Like all body cells, also spermatozoa comprise a cell-type-typical proteome, i.e., various molecular structures typical for this specific cell type, not excluding that other cell types may comprise partly the same molecular structures. Several molecular structures are known as biomarkers somewhat associated with fertility of spermatozoa.

A further protein that occurs predominantly on few cell types including spermatozoa is Vimentin (Vim). Vimentin positivity is currently expressed in the head domain of sperms. An asymptomatic distribution in sperms correlates with the different structural defects of sperm (Markova et al., 2002, Folia Biol (Praha), 48:160-162). Markers for male fertility are also described in WO 1997/040386.

It is known that Vimentin filaments may be disrupted by some phthalate esters such as di(n-butyl) phthalate (cf., Alam et al., 2010, Anat Histol Embryol. 39(3):186-193). The occurrence of Vimentin had also been investigated in subfertile spermatozoa (Marinova et al., 1996, Andrologia 28(5):287-289). It was however noted that full length Vimentin is no suitible marker for fertility as its absence is merely typical for some types of infertility.

The Vimentin splice variant Vimentin variant 3 (Vim3) was described in the context of kidney cancer diagnosis (von Brandenstein et al., 2015, Disease Markers, Article ID 368534. doi: 10.1155/2015/368534). WO 2005/121803 teaches dipstick tests usable in the context of measurements of cytoskeletal proteins.

There is still an unmet need for a method for determining the fertility of spermatozoa that is easily conductible, reliable and also works with stored and/or frozen samples.

Surprisingly, it was found that determining the total content and/or localization of the Vimentin variant 3 (Vim3) of the spermatozoa is well suitable for determining the fertility of said spermatozoa. A method based on this finding is technically particularly efficient and is surprisingly also comparably reliable for stored spermatozoa samples.

In a first aspect, the present invention relates to a method for determining the fertility of spermatozoa contained in a sample S, said method comprising detecting the total content of the Vimentin variant 3 (Vim3) per spermatozoon and/or the spatial localization of the Vim3 within the stained spermatozoa.

In a preferred embodiment, the method is an in vitro method. Detecting may be understood in the broadest sense and may be conducted by any means. As described in more detail below, there are various means for detecting available in the art.

For example, detecting may be conducted by microscopic means such as, e.g., by microscopic imaging of spermatozoa in a sample S in which Vim3 may be stained.

In a preferred embodiment, the method comprises the following steps:
(i) optionally providing an aliquot of the sample S containing spermatozoa;
(ii) optionally staining Vim3 in the spermatozoa contained in the sample S;
(iii) detecting the total content of the Vim3 per spermatozoon and/or the spatial localization of the Vim3 within the stained spermatozoa, wherein the Vim3 is optionally stained Vim3 of step (ii); and
(iv) determining the total content of Vim3 per spermatozoon and/or the degree of accumulation of Vim3 in the mid piece, more in particular the neck region of the spermatozoa.

Herein, a decreased amount of the total content of Vim3 per spermatozoon contained in the sample S and/or a decreased amount of accumulation of Vim3 in the mid piece, more in particular the neck region, of the spermatozoa contained in the sample S may indicate decreased fertility of the spermatozoa contained in the sample S. These amounts may optionally be compared with one or more healthy spermatozoa (normozoospermia) and/or one or more control samples C+ of spermatozoa of high fertility of the same species and/or one or more control sample C− of spermatozoa of low fertility of the same species.

As described in more detail below, determining total content of Vim3 per spermatozoon and/or the degree of accumulation of Vim3 may be conducted by various means. For example, this step may be conducted by means of microscopy, optionally combined with staining Vim3, but also by means of mass spectrometry and/or immunochemical means, etc., optionally combined with staining Vim3.

In a preferred embodiment, the present invention relates to a method for determining the fertility of spermatozoa contained in a sample S, said method comprising the following steps:
(i) optionally providing an aliquot of the sample S containing spermatozoa;
(ii) optionally staining Vimentin variant 3 (Vim3) in the spermatozoa contained in the sample S;
(iii) detecting the total content of the Vim3 per spermatozoon and/or the spatial localization of the Vim3 within the stained spermatozoa, wherein the Vim3 is optionally stained Vim3 of step (ii);
(iv) determining the total content of Vim3 per spermatozoon and/or the degree of accumulation of Vim3 in the mid piece, more in particular the neck region of the spermatozoa; and
(v) comparing the total content of Vim3 per spermatozoon and/or the degree of accumulation of Vim3 determined in step (iv) between the sample S and
    (a) at least one control sample C+ of spermatozoa of high fertility of the same species, and/or
    (b) at least one control sample C− of spermatozoa of low fertility of the same species,
wherein
    a decreased amount of the total content of Vim3 per spermatozoon contained in the sample S in comparison to the control sample C+;
    an amount of the total content of Vim3 per spermatozoon contained in the sample S that is not higher than in the control sample C−;
    a decreased amount of accumulation of Vim3 in the mid piece, more in particular the neck region, of the spermatozoa contained in the sample S in comparison to the control sample C+; and/or
    an amount of accumulation of Vim3 in the mid piece, more in particular the neck region, of the spermatozoa contained in the sample S that is not higher than in the control sample C−,
indicates decreased fertility of the spermatozoa contained in the sample S.

In other words, a decreased amount of the total content of Vim3 per spermatozoon contained in the sample S in comparison to the control sample C+ and/or C−, and/or a decreased amount of accumulation of Vim3 in the mid piece, more in particular the neck region, of the spermatozoa contained in the sample S in comparison to the control sample C+ and/or C− indicates decreased fertility of the spermatozoa contained in the sample S.

One or both of the control samples C+ and C− may serve as reference point(s) when the fertility of such sample(s) is known.

The person skilled in the art will notice that the method of the present invention preferably is an in vitro method, i.e., preferably a method not directly associated with the diagnosis of the human or animal body. The results may be used for medicinal or non-medicinal purposes. The sample S typically is an in vitro specimen, i.e., a specimen remote from the human and animal body.

In a preferred embodiment, comparison is comparison between the sample S and at least one control sample C+ of spermatozoa of high fertility of the same species (option (a)).

The method of the present invention may be conducted in that it comprises steps (i) and (ii) as above followed by steps (iii)-(v):
(iii) detecting the localization of the Vim3 within the spermatozoa, wherein the Vim3 is optionally stained Vim3 of step (ii);
(iv) determining the degree of accumulation of Vim3 in the mid piece, more in particular the neck region, of the spermatozoa; and
(v) comparing the degree of accumulation of Vim3 determined in step (iv) between the sample S and
   (a) at least one control sample C+ of spermatozoa of high fertility of the same species, and/or
   (b) at least one control sample C− of spermatozoa of low fertility of the same species,
wherein
a decreased amount of accumulation of Vim3 in the mid piece, more in particular the neck region, of the spermatozoa contained in the sample S in comparison to the control sample C+; and/or
an amount of accumulation of Vim3 in the mid piece, more in particular the neck region, of the spermatozoa contained in the sample S that is not higher than in the control sample C−,
indicates decreased fertility of the spermatozoa contained in the sample S.

Alternatively or additionally, the method of the present invention may be conducted in that it comprises steps (i) and (ii) as above followed by steps (iii)-(v):
(iii) detecting the total content of Vim3 per spermatozoon, wherein the Vim3 is optionally stained Vim3 of step (ii);
(iv) determining the total content per spermatozoon of the Vim3; and
(v) comparing the total content of Vim3 per spermatozoon determined in step (iv) between the sample S and
   (a) at least one control sample C+ of spermatozoa of high fertility of the same species, and/or
   (b) at least one control sample C− of spermatozoa of low fertility of the same species,
wherein
a decreased amount of the total content of Vim3 per spermatozoon contained in the sample S in comparison to the control sample C+; and/or
an amount of the total content of Vim3 per spermatozoon contained in the sample S that is not higher than in the control sample C−,
indicates decreased fertility of the spermatozoa contained in the sample S.

Most preferably, the method of the present invention may be conducted in that it comprises steps (i) and (ii) as above followed by steps (iii)-(v):
(iii) detecting the localization and (concomitantly) total content per spermatozoon of the Vim3 within the stained spermatozoa, wherein the Vim3 is optionally stained Vim3 of step (ii);
(iv) determining the degree of accumulation of Vim3 in the mid piece, more in particular the neck region, and (concomitantly) total content of Vim3 per spermatozoon of the spermatozoa; and
(v) comparing the degree of accumulation of Vim3 and (concomitantly) total content of Vim3 per spermatozoon determined in step (iv) between the sample S and
   (a) at least one control sample C+ of spermatozoa of high fertility of the same species, and/or
   (b) at least one control sample C− of spermatozoa of low fertility of the same species,
wherein
a decreased amount of the total content of Vim3 per spermatozoon contained in the sample S in comparison to the control sample C+; and/or an amount of the total content of Vim3 per spermatozoon contained in the sample S that is not higher than in the control sample C−,
and (concomitantly),
a decreased amount of accumulation of Vim3 in the mid piece, more in particular the neck region, of the spermatozoa contained in the sample S in comparison to the control sample C+; and/or an amount of accumulation of Vim3 in the mid piece, more in particular the neck region, of the spermatozoa contained in the sample S that is not higher than in the control sample C−,
indicates decreased fertility of the spermatozoa contained in the sample S.

In a preferred embodiment, the amount of accumulation of Vim3 in the mid piece, more in particular the neck region, of the spermatozoa is accompanied by the colocalization of Vim3 and mitochondria. Therefore, the method of the present invention may also comprise determining the degree of colocalization of Vim3 and mitochondria.

In a preferred embodiment, thus, the method may, in addition to steps (i)-(iii) as described above, comprise the following steps (iv) and (v), optionally combined with alternative steps as described herein:
(iv) determining the degree of colocalization of Vim3 and mitochondria; and
(v) degree of colocalization of Vim3 and mitochondria determined in step (iv) between the sample S and
   (a) at least one control sample C+ of spermatozoa of high fertility of the same species, and/or
   (b) at least one control sample C− of spermatozoa of low fertility of the same species,
wherein
a decreased degree of colocalization of Vim3 and mitochondria in the spermatozoa contained in the sample S in comparison to the control sample C+; and/or
a degree of colocalization of Vim3 and mitochondria in the spermatozoa contained in the sample S that is not higher than in the control sample C−, indicates decreased fertility of the spermatozoa contained in the sample S.

Optionally, step (iv) of determining the degree of colocalization of Vim3 and mitochondria may be accompanied by cutting off the head and tail regions from the neck region of the spermatozoa, e.g., by means of Laser-based microdissection. This may further improve accuracy of the determination of the colocalization. Determining the degree of colocalization of Vim3 and mitochondria may be conducted by any means, in particular by means of microscopy such as, e.g., fluorescence microscopy.

It was surprising found that an agent such as Vim3 protein could be easily and predominantly detected in normozoosperim e.g. by immune staining (e.g., immunofluorescence), flow cytometry (also designated as fluorescence activated cell sorting (FACS) analysis, herein understood interchangeably), making the detection of Vim3 a specific marker for ejaculates from man with normozoospermia. Vim3 protein was identified in sperms with different morphological aspects (i.e. normozoospermia, OAT syndrome, azoospermia). By immunofluorescence analysis, Vim3 was abundant in normozoospermia but low in samples from patients with OAT syndrome. The reverse pattern was observed for full length Vimentin.

Accordingly, additionally or alternatively to a decreased amount of the total content and/or accumulation of Vim3 in spermatozoa as described above, also the an increased amount of the total content and/or accumulation of Vimentin in general (including the full length Vimentin) in spermatozoa may serve as an indicator of decreased fertility of the spermatozoa contained in the sample S.

Accordingly, in a preferred embodiment, in addition to steps (i) to (v) according to the present invention, the method comprises the further steps of:
- (ii-b) optionally staining Vimentin in general (including the full length Vimentin) in the spermatozoa contained in the sample S;
- (iii-b) detecting the total content of the Vimentin in general per spermatozoon and/or the spatial localization of the Vimentin in general within the stained spermatozoa, wherein the Vimentin in general is optionally stained Vim3 of step (ii);
- (iv-b) determining the total content of Vimentin in general per spermatozoon and/or the degree of accumulation of Vimentin in general in the mid piece, more in particular the neck region of the spermatozoa; and
- (v-b) comparing the total content of Vimentin in general per spermatozoon and/or the degree of accumulation of Vim3 determined in step (iv) between the sample S and
  - (a) at least one control sample C+ of spermatozoa of high fertility of the same species, and/or
  - (b) at least one control sample C− of spermatozoa of low fertility of the same species, wherein
a decreased amount of the total content of Vim3 per spermatozoon contained in the sample S in comparison to the control sample C+;
an amount of the total content of Vim3 per spermatozoon contained in the sample S that is not higher than in the control sample C−;
a decreased amount of accumulation of Vim3 in the mid piece, more in particular the neck region, of the spermatozoa contained in the sample S in comparison to the control sample C+; and/or
an amount of accumulation of Vim3 in the mid piece, more in particular the neck region, of the spermatozoa contained in the sample S that is not higher than in the control sample C−,
indicates decreased fertility of the spermatozoa contained in the sample S.

In other words,
a decreased amount of the total content of Vim3 per spermatozoon contained in the sample S in comparison to the control sample C+;
an amount of the total content of Vim3 per spermatozoon contained in the sample S that is not higher than in the control sample C−;
a decreased amount of accumulation of Vim3 in the mid piece, more in particular the neck region, of the spermatozoa contained in the sample S in comparison to the control sample C+;
an amount of accumulation of Vim3 in the mid piece, more in particular the neck region, of the spermatozoa contained in the sample S that is not higher than in the control sample C−;
each or a combination of two or more thereof may indicate decreased fertility of the spermatozoa contained in the sample S.

Determining the fertility of spermatozoa may be understood in the broadest sense as any assessment of the degree of suitability of the spermatozoa for sexual reproduction by natural or artificial insemination. Accordingly, the degree of fertility also includes the mobility and vitality of the spermatozoa. The determination of spermatozoa as being infertile or less fertile does not exclude sexual reproductive capability by fusing a spermatozoon with an ovule artificially in vitro, in particular by injecting the genetic material into the ovule (in vitro fertilization in a test tube) because in such process no mobility and viability of the latter is required.

The expression of Vim3 was found (significantly) higher in ejaculates from patients with normozoospermia (control sample C+), whereas in ejaculates from patients with oligo-astheno-teratozoospermia (OAT syndrome) and azoospermia the expression of Vim3 was significantly decreased. Moreover, full length Vimentin expression was detectable in normozoospermia as well as in the OAT syndrome, but was absent in ejaculates from patients with azoospermia. Therefore, the method of the present invention is also suitable for distinguishing different causes of infertility.

In the method of the present invention, a decreased amount of accumulation of Vim3 in the mid piece, more in particular the neck region, of the spermatozoa contained in the sample S in comparison to the control sample C+, wherein Vimentin full length (e.g., V9) is expressed in both samples S and C+, may indicate OAT syndrome.

The term "spermatozoon", "sperm", "spermatozoon cell", "sperm cell" and the like may be understood interchangeably in the common sense in the art, i.e., as a, preferably matured, male gamete.

In the method of the present invention, a decreased amount of accumulation of Vim3 in the mid piece, more in particular the neck region, of the spermatozoa contained in the sample S in comparison to the control sample C+, wherein Vimentin full length (e.g., V9) is expressed in control sample C+, but is diminished or (essentially) absent in sample S, may indicate azoospermia. In other words, the absence, decreased amount or misdistribution of full length Vimentin (V9) in the sample S is indicative for morphological changes of the sperm and thus indicates low fertility. In a preferred embodiment, the detection of the distribution or misdistribution of the full length Vimentin protein by using full length Vimentin protein-specific antibody (e.g. the one used for the examples) which are well known in the art and available from commercial suppliers.

The control sample C− of spermatozoa of low fertility may preferably obtained from a patient of the same species suffering from oligozoospermia, asthenozoospermia and/or teratozoospermia, or oligo-astheno-teratozoospermia (OAT syndrome) and/or azoospermia and/or any other pathologic state accompanied by low fertility of the spermatozoa, in particular oligozoospermia, asthenozoospermia and/or teratozoospermia.

As used herein, a total content per spermatozoon may be understood in the broadest sense as the content of the respective polypeptide (e.g., Vim3) in the cells. It will be understood that typically not the amount of polypeptide comprised in one spermatozoon is determined, but typically the average of a larger number of spermatozoa. As it is well-known that all spermatozoa of a sample S will generally each have (essentially) the same weight, the determination of the total content per spermatozoon is equivalent to the total content per spermatozoon weight. The reference "per spermatozoon" or "per spermatozoa weight" or the like normalizes different samples (e.g., samples S and C+ and/or C−) and makes them comparable with another, independent on the total number or concentration of spermatozoa comprised in the respective sample. Alternatively, also the content of Vim3 per milliliter of the sample S or the content of Vim3 per milligram of the sample S can be determined, when the spermatozoa content is comparable in the different samples (e.g., samples S and C+ and/or C−) to be compared with another. Then, exemplarily, the amount of Vim3 can be determined per volume and/or weight of ejaculate.

As used herein, "decreased amount" may be understood in the broadest sense as lower degree. Typically, a decreased amount is a degree that is at least 10%, at least 20%, at least 50%, at least 75%, at least 2-fold, 3-fold, 4-fold, 5-fold, 6-fold, 7-fold, 8-fold, 9-fold or 10-fold lower than the value it is compared with (e.g., that of the control sample C+).

As used herein, "not higher than" in the context of comparison with control sample C− may be understood in the broadest sense as not being significantly higher, i.e., not 10% higher, in particular equal or lower than the value it is compared with (e.g., that of the control sample C−).

When exemplarily fluorescence detection is used, the decreased amount may refer to the decrease of the intensity of the fluorescence signal (detectable under the same measurement conditions). When exemplarily fluorescence microscopy is used, the decreased amount may refer to the decrease of the intensity of the local fluorescence signal (detectable under the same measurement conditions for the neck or tail regains of the spermatozoa). When exemplarily flow cytometry (also designated as fluorescence activated cell sorting (FACS), herein understood interchangeably) is used, the decreased amount may refer to the decrease of the intensity of the mean fluorescence signal (detectable under the same measurement conditions for the spermatozoa).

The aliquot of the sample S containing the spermatozoa may be any specimen comprising one or more spermatozoa. The aliquot may comprise the whole sample S or may be, preferably, a part thereof. The spermatozoa may be viable or may be fixed, i.e., dead. The sample S may be liquid, pasty or solid. It may be tissue sample, a solid sample, a liquid sample, a cell sample, tissue section etc. Suitable methods for obtaining a sample are known in the art and include the masturbation, a testis biopsy, or other common methods used in the art. A sample S comprising viable spermatozoa will typically be liquid or pasty and will (essentially) consist of spermatozoa and ingredients not harmful to the spermatozoa in the present concentrations. A fixed sample S may optionally also be solid. Optionally, the sample S is placed on a specimen carrier, preferably a transparent specimen carrier, in particular a microscopic slide or a well of a multiwell plate.

Exemplarily, the sample S may be an ejaculate or a processed ejaculate or an aliquot thereof. A processed ejaculate may optionally be diluted in an aqueous buffer and/or in an organic liquid.

Alternatively, the sample S may be a testis biopsy (e.g., obtained in the context of testicular sperm extraction (TESE)). This may exemplarily be stained (e.g., by means of a Vim3-specific antibody or antibody fragment that is labelled (e.g., by a fluorescence and/or color dye or a metal particle (e.g., a gold bead)) or an unlabeled Vim3-specific antibody or antibody fragment that is bound by a labeled secondary antibody). Then, the method of the present invention may be an immunohistological method. The experimenter may compare the signal intensity found (in the relevant parts containing spermatozoa and precursors thereof) of the testis biopsy of a patient of interest with a comparable testis sample of a well-fertile individual of the same species. Such staining also allows the localization of Vim3 in situ. In principle, the use of a radioactively labeled Vim3-specific antibody or antibody fragment may be even used in vivo to localize the Vim3 within the body.

Vimentin variant 3 (Vim3) (also referred to as Vimentin3, Vimentin variant 3, Vimentin splice form 3) is a splice isoform of Vimentin. Vim3 in the context of the present invention may be any Vim3 compound. Vimentin itself is an intermediate sized filament that functions in signal transduction cellular function, structural integrity of cells and tissues and adhesion and migration. In 2007, a variant of Vimentin (Vim3) was described by a working group of the Craig Venter Institute (NHLBI Resequencing and Genotyping Service (RSG), N01-NV-48196, J. Craig Venter Institute, Rockville, Md. 20850). In 2011, the presence of this Vim3 in gliomas was described (Thakkar et al., 2011, Cancer Invest 29:113-122). Vim3 is a spliced variant of Vimentin with a unique C-terminal ending. Preferably, Vim3 is the naturally occurring Vim3 of the species of interest, i.e., the Vim3 occurring in the spermatozoa comprised in the sample S. Exemplarily, Vim3 may be human Vim3 or Vim3 of a non-human animal (e.g., a non-human mammal (e.g., an domestic mammal (e.g., a bovine, a pig, a horse, a donkey, a sheep, a goat, a dog, a cat, etc.) or another animal intended for propagation (e.g., an endangered species (e.g., a tiger, an elephant, etc.)). Vim3 has been found in numerous species so far.

In a preferred embodiment, Vim3 is human Vim3. The human splice variant Vim3 is has 421 amino acids and is 35 amino acids smaller than the full length protein. Its unique structure leads to a 10 kDa smaller protein. The amino acid sequence of human Vim3 has been published and is available at UniProt KB (http://www.uniprot.org/uniprot/B0YJC4) or at the National Center for Biotechnology Information under GenBank Accession number ACA06103.1 (http://www.ncbi.nlm.nih.gov/protein/167887751). Preferably, in the context of the present invention, Vim3 has a homology of at least 80%, more preferably at least 90%, even more preferably at least 95%, even more preferably at least 98%, even more preferably at least 99% of SEQ ID NO: 1, in particular is identical with SEQ ID NO: 1:

```
 1  mstrsvssss yrrmfggpgt asrpsssrsy vttstrtysl gsalrpstsr slyasspggv
61  yatrssavrl rssvpgvrll qdsvdfslad aintefkntr tnekvelqel ndrfanyidk
```

```
121  vrfleqqnki  llaeleqlkg  qgksrlgdly  eeemrelrrq  vdqltndkar  veverdnlae 181  dimrlreklq  eemlqreeae  ntlqsfrqdv  dnaslarldl  erkveslqee  iaflkklhee 241  eiqelqaqiq  eqhvqidvdv  skpdltaalr  dvrqqyesva  aknlqeaeew  ykskfadlse 301  aanrnndalr  qakqesteyr  rqvqsltcev  dalkgtnesl  erqmremeen  faveaanyqd 361  tigrlqdeiq  nmkeemarhl  reyqdllnvk  maldieiaty  rkllegeesr  islplpnfss 421  lnlrgkhfis  l
```

In an alternative preferred embodiment, Vim3 is mammalian non-human Vim3 such as, e.g., bovine Vim3, pig Vim3, horse Vim3, donkey Vim3, sheep Vim3, goat Vim3, dog Vim3, or cat Vim3. The Vimentin sequence of other species is also known, including e.g. *Mus musculus* (NCBI Accession: CAA39807.1, NP_035831.2), *Rattus norvegicus* (NCBI Accession: NP_112402.1), *Bos taurus* (NCBI Accession: NP_776394.2), *Gallus gallus* (NCBI Accession: NP_001041541.1), *Mesocricetus auratus* (Accession: AAA37104.1), *Oncorhynchus mykiss* (Accession: CAA90601.1), *Equus caballus* (NP_001230074.1), *Salmo salar* (Accession: NP_001133947.1), *Pan troglodytes* (Accession: NP_001009148.1) and *Cavia porcellus* (Accession: NP_001166511.1). The splice variant corresponding to human Vim3 could be easily identified by sequence analysis and identification of homologues.

Protein expression of Vimentin described in the literature by immune histology results from the combined detection not only of the protein from full length but also of the spliced variant Vim3. Therefore, Vimentin positivity is not an accurate differentiation feature of deformed sperms due to the spliced Vim3 being detectable with the currently used antibodies against the.

The method of the present invention may be conducted immediately after obtaining the sample S (i.e., within the first hour after the donor has ejaculated, and thus provided the sperm donation) or may be conducted later such as, e.g., between 1 and 5 hours, between 2 and 10 hours, between 5 and 24 hours, between 12 hours and 2 days, between 2 and 7 days, between 1 and 4 weeks, between 1 and 12 months or after more than 1 year. The method may be conducted in a sample S of fixed or viable spermatozoa.

In a preferred embodiment, step (ii) of staining intracellular Vim3 comprises the fixation of the spermatozoa contained in the sample S prior to staining the intracellular Vim3 in the spermatozoa.

Fixation may bear the technical advantage that the sample S may optionally be stored for longer still enabling sufficient readout. Optionally, then the sample S may also be stored in a dried state. Further, handling is considerably easier. Exemplarily, compounds used for staining of (optional) step (ii) do not necessarily have to be cell-penetrating and non-toxic. Upon fixation, the cell membranes may optionally also be rendered permeably for larger sized compounds such as, e.g., antibodies or antibody fragments. Likewise, also toxic agents may be used for staining without disturbing the results.

Fixation may be performed by any means known in the art. Exemplarily, fixation may be performed by adding formaldehyde, methanol and/or ethanol to a solution comprising the spermatozoa of interest.

Step (ii) of staining intracellular Vim3 may be understood in the broadest sense as labelling the intracellular Vim3 by any detectable means. Preferably, detecting of step (iii) is determination of the localization of Vim3 in the spermatozoa. Therefore, detection is preferably detection by any imaging method (e.g., by microscopy). Alternatively, detection may also be detection of radioactivity.

In order to enable detecting (step (iii), the Vim3 is preferably labeled. Therefore, Vim3 is either detectably as such or, more preferably, is bound by a labeled marker. As used herein, the term "labeled marker" may be understood in the broadest sense as any compound specifically binding to Vim3 that is detectable by any means.

Preferably, but not necessarily, a labeled marker comprises two moieties conjugates with another, i.e., at least one binding moiety is conjugated with at least one label moiety. More preferably, a binding moiety and a label moiety are covalently conjugated with another, either directly of via a spacer.

As used throughout the present invention, the term "conjugated with" may be understood in the broadest sense as any kind of covalent or non-covalent attachment or linkage of one component with another component, preferably via a covalent linkage. It is not limited to a specific kind of formation of a conjugate. Depending on the components conjugated with another, such conjugate can be obtained by chemical means and/or by genetic engineering and biotechnological means.

Accordingly, a labeled marker may optionally comprise one or more binding moieties specifically binding to Vim3 and one or more label moieties. Preferably, a labeled marker comprises one binding moiety specifically binding to Vim3 and one label moiety. Alternatively, the binding moiety is detectably by itself.

The label moiety may be any moiety that is detectable, preferably detectable by an imaging method.

In a preferred embodiment, step (ii) of staining intracellular Vim3 is staining with a fluorescently labeled marker.

As used herein, the term "fluorescence labeled marker" may be understood in the broadest sense as any compound specifically binding to Vim3 that is either fluorescent (by itself) or is conjugated with a fluorescence unit.

Preferably, a fluorescence marker comprises one or more binding moieties specifically binding to Vim3 and one or more fluorescent label moieties. More preferably, a fluorescently labeled marker comprises one binding moiety specifically binding to Vim3 and one fluorescence labeled moiety. More preferably, the binding moiety and the fluorescent label moiety are covalently conjugated with another, either directly of via a spacer. Alternatively, the binding moiety is fluorescent by itself.

As used in the context of the present invention, a fluorescent label moiety may be any fluorescent moiety known in the art. Exemplarily, a fluorescent label moiety may be a fluorescent polypeptide moiety (e.g., cyan fluorescent protein (CFP), green fluorescent protein (GFP) or yellow fluorescent protein (YFP), red fluorescent protein (RFP), mCherry, etc.), a small-molecule dye moiety (e.g., an Atto dye moiety (e.g., ATTO 390, ATTO 425, ATTO 465, ATTO 488, ATTO 495, ATTO 520, ATTO 532, ATTO 550, ATTO 565, ATTO 590, ATTO 594, ATTO 610, ATTO 611X, ATTO 620, ATTO 633, ATTO 635, ATTO 637, ATTO 647, ATTO 647N, ATTO 655, ATTO 665, ATTO 680, ATTO 700, ATTO 725, ATTO 740), a Cy dye moiety (e.g., Cy3, Cy5, Cy5.5, Cy 7), an Alexa dye moiety (e.g., Alexa Fluor 488, Alexa Fluor 546, Alexa Fluor 647, Alexa Fluor 680, Alexa Fluor 750), a VisEn dye moiety (e.g. VivoTag680, VivoTag750), an S dye (e.g., S0387), a DyLight fluorophore moiety (e.g., DyLight 750, DyLight 800), an IRDye moiety (e.g., IRDye 680, IRDye 800), a fluorescein dye moiety (e.g., fluorescein, carboxyfluorescein, fluorescein isothiocyanate (FITC)), a rhodamine dye moiety (e.g., rhodamine, tetramethylrhodamine (TAMRA)), a HOECHST dye moiety, a quantum dot moiety or a combination of two or more thereof. Such fluorescent label moiety may be used in fluorescence microscopy.

Alternatively or additionally, the label moiety may be metal atom, metal ion or metal bead (e.g., a (colloidal) gold such as a gold bead). Such metal bead may be used in electron microscopy.

Alternatively or additionally, the label moiety may be radioactive label such as, e.g., $^{3}H$, $^{14}C$, $^{123}I$, $^{124}I$, $^{131}I$, $^{32}P$, $^{99m}Tc$ or lanthanides (e.g., $^{64}Gd$). In this context, a radioactive label may or may not be suitable for scintillation assays, computer tomography (CT), single-photon emission computed tomography (SPECT) or as a label suitable for Positron Emission Tomography (PET) (e.g., $^{11}C$, $^{13}N$, $^{15}O$, $^{18}F$, $^{82}Rb$). Then, the spermatozoa are optionally harvested, fragmented in their subunits and the subunits fragmented (e.g., by (ultra) centrifugation). Then, the amount of radioactivity in the various fractions may be detected.

It will be understood that, the detecting step (iii) will depend on the chosen label moiety for staining (step (ii)). As mentioned above, detecting is preferably performed by an imaging method. Particularly preferred is detecting the localization of the Vim3.

Accordingly, in a highly more preferred embodiment, step (ii) of staining intracellular Vim3 is staining with a fluorescently labeled marker and step (iii) is detecting the localization of the Vim3 conducted by fluorescence microscopy.

The binding moiety (also: molecular or chemical entity or substance) may be any moiety specifically binding to Vim3. The binding moiety may be a high molecular weight compound of a molecular weight of 5 kDa or more or may be small molecule of a molecular weight of less than 5 kDa. Preferably, the binding moiety is a high molecular weight compound of a molecular weight of 5 kDa or more, more preferably of more than 10 kDa, even more preferably of more than 20 kDa, even more preferably of more than 50 kDa and even more preferably of more than 100 kDa. Exemplarily, the binding moiety may be a polypeptide, a polysaccharide or a synthetic agent (e.g., a small molecule drug) each optionally conjugated with a synthetic polymer (e.g., methacrylate (MA), hydroxypropyl methacrylate (HPMA), polylactic acid (PLA), polyglycolic acid (PGA), polyethylene glycol (PEG), polylysine (PL)) or a combination of two or more thereof. Preferably, the binding moiety is a polypeptide. More preferably, the binding moiety is an antibody or a mutant or fraction thereof.

In a preferred embodiment, step (ii) of staining intracellular Vim3 comprises binding of a Vim3-specific antibody or antibody fragment, preferably a labeled Vim3-specific antibody or antibody fragment, in particular a Vim3-specific antibody or antibody fragment labeled by a fluorescent label or a (colloidal) gold label.

As used in the context of the present invention, the term "antibody" may be understood in the broadest sense as any type of immunoglobulin or antigen-binding fraction or mutant thereof known in the art.

Exemplarily, the antibody of the present invention may be an immunoglobulin A (IgA), immunoglobulin D (IgD), immunoglobulin E (IgE), immunoglobulin G (IgG), immunoglobulin M (IgM), immunoglobulin Y (IgY) or immunoglobulin W (IgW). Preferably, the antibody is an IgA, IgG or IgD. More preferably, the antibody is an IgG. However, it will be apparent that the type of antibody may be altered by biotechnological means by cloning the gene encoding for the antigen-binding domains of the antibody of the present invention into a common gene construct encoding for any other antibody type.

The binding between the antibody and its molecular target structure (i.e., its antigen, e.g., Vim3) typically is a non-covalent binding. Preferably, the binding affinity of the antibody to its antigen has a dissociation constant (Kd) of less than 1 µM, less than 500 nM, less than 200 nM, less than 100 nM, less than 50 nM, less than 40 nM, less than 30 nM or even less than 20 nM.

The term "antibody" as used herein may be understood in the broadest sense and also includes what may be designated as an antibody mutant. As used in the context of the present invention, an antibody mutant may be understood in the broadest sense as any antibody mimetic or antibody with altered sequence known in the art. The antibody mutant may have at least 10%, at least 20%, at least 50%, at least 60%, at least 70%, at least 80%, at least 85%, at least 90% or at least 95% of the binding affinity of a corresponding antibody, i.e., bear a dissociation constant (Kd) of less than 10 µM, less than 1 µM, less than 500 nM, less than 200 nM, less than 100 nM, less than 50 nM, less than 40 nM, less than 30 nM or even less than 20 nM.

As used herein, the term "antibody fragment" may be understood in the broadest sense as any fragment of an antibody that still bears binding affinity to its molecular target (i.e., its antigen, e.g., Vim3). Exemplarily, the antibody fragment may be a fragment antigen binding (Fab fragment), Fc, F(ab')$_2$, Fab', scFv, a truncated antibody comprising one or both complementarity determining region(s) (CDR(s)) or the variable fragment (Fv) of an antibody. Variable domains (Fvs) are the smallest fragments with an intact antigen-binding domain consisting of one $V_L$ and one $V_H$. Such fragments, with only the binding domains, can be generated by enzymatic approaches or expression of the relevant gene fragments, e.g. in bacterial and eukaryotic cells. Different approaches can be used, e.g. either the Fv fragment alone or 'Fab'-fragments comprising one of the upper arms of the "Y" that includes the Fv plus the first constant domains. These fragments are usually stabilized by introducing a polypeptide link between the two chains which results in the production of a single chain Fv (scFv). Alternatively, disulfide-linked Fv (dsFv) fragments may be used. The binding domains of fragments can be combined with any constant domain in order to produce full length antibodies or can be fused with other proteins and polypeptides. A recombinant antibody fragment is the single-chain Fv (scFv) fragment. Dissociation of scFvs results in monomeric scFvs, which can be complexed into dimers (diabodies), trimers (triabodies) or larger aggregates such as TandAbs and Flexibodies. The antibody may be a Fab, a Fab', a F(ab')2, a Fv, a disulfide-linked Fv, a scFv, a (scFv)$_2$, a bivalent antibody, a bispecific antibody, a multispecific antibody, a diabody, a triabody, a tetrabody or a minibody.

As mentioned above, the term "antibody" may also include an antibody mimetic which may be understood in the broadest sense as organic compounds that, like antibodies, can specifically bind antigens and that typically have a molecular mass in a range of from approximately 3 kDa to approximately 25 kDa. Antibody mimetics may be, e.g., affibody molecules (affibodies), affilins, affitins, anticalins, avimers, DARPins, Fynomers, Kunitz domain peptides, single-domain antibodies (e.g., VHH antibodies or VNAR antibodies, nanobodies), monobodies, diabodies, triabodies, flexibodies and tandabs. The antibody mimetics may be of natural origin, of gene technologic origin and/or of synthetical origin. The antibody mimetics may also include polynucleotide-based binding units. Optionally, the antibody may also be a CovX-body. Optionally, the antibody may also be a cameloid species antibody.

In a preferred embodiment, in the context of Vim3, the antibody or antibody fragment is selective for Vim3. More preferably, in the context of Vim3, the antibody or antibody fragment binds to Vim3 with an at least 10-fold, even more preferably at least 100-fold, even more preferably at least 1000-fold higher binding affinity than to full-length Vimentin (V9). In a particularly preferred embodiment, the antibody or antibody fragment binds to the unique C-terminal 8 amino acids of Vim3 (RGKHFISL: SEQ ID No: 2). This is further exemplified in WO 2014/154686 and in the example section.

The antibody according to the present invention is preferably a monoclonal antibody, a chimeric antibody or a humanized antibody. Monoclonal antibodies are monospecific antibodies that are identical because they are produced by one type of immune cell that are all clones of a single parent cell. A chimeric antibody is an antibody in which at least one region of an immunoglobulin of one species is fused to another region of an immunoglobulin of another species by genetic engineering in order to reduce its immunogenicity. For example murine $V_L$ and $V_H$ regions may be fused to the remaining part of a human immunoglobulin. A particularly preferred type of chimeric antibodies are humanized antibodies. Humanized antibodies are produced by merging the DNA that encodes the CDRs of a non-human antibody with human antibody-producing DNA. The resulting DNA construct can then be used to express and produce antibodies that are usually not as immunogenic as the non-human parenteral antibody or as a chimeric antibody, since merely the CDRs are non-human.

The antibody or antibody fragment, independent on its chemical nature, may optionally be dissolved in any medium suitable for storing said antibody such as, e.g., water, an aqueous buffer (e.g., a Hepes, Tris, or phosphate buffer (e.g. phosphate buffered saline (PBS)), an organic solvent (e.g., dimethyl sulfoxide (DMSO), dimethylformide (DMF)) or a mixture of two or more thereof. The antibody or mutant thereof according to the present invention may be of any species or origin. It may bind to any epitope(s) comprised by its molecular target structure (e.g., linear epitope(s), structural epitope(s), primary epitope(s), secondary epitope(s), e.g., such of Vim3). Preferably, the antibody or mutant thereof may recognize the naturally folded molecular target structure or a domain or fragment thereof (e.g., Vim3 in its natural environment inside the spermatozoa). The antibody or mutant thereof may be of any origin an antibody may be obtained from such as, e.g., natural origin, a gene technologic origin and/or a synthetic origin. Optionally, the antibody may also be commercially available. The person skilled in the art will understand that the antibody may further comprise one or more posttranscriptional modification(s) and/or may be conjugated to one or more further structures such as label moieties or cell-penetrating peptides (CPPs). Optionally, the antibody or antibody fragment may be added to a support, particularly a solid support such as an array, bead (e.g. glass or magnetic), a fiber, a film etc. The skilled person will be able to adapt the antibody of the present invention and a further component to the intended use by choosing a suitable further component.

Detection by means of antibodies may base on direct or indirect immunodetection. Accordingly, in a preferred embodiment, step (ii) of staining intracellular Vim3 comprises:

(iia) direct immunodetection comprising providing at least one Vim3-specific labeled antibody or antibody fragment (said "labeled antibody or antibody fragment" also designated as "AB1-L"), and
enabling the binding of said AB1-L to the intracellular Vim3 in the spermatozoa; or (iib) indirect immunodetection comprising providing at least one Vim3-specific unlabeled antibody or antibody fragment (said "unlabeled antibody or antibody fragment" also designated as "AB1-ul") and at least one labeled antibody or antibody fragment (said "labeled antibody or antibody fragment" also designated as "AB2-L") specifically binding to AB1-ul,
enabling the binding of AB1-ul to the intracellular Vim3 in the spermatozoa, and
enabling the binding of AB2-L to AB1-ul.

In a particularly preferred embodiment, in this context, immunodetection is immunofluorescence and the labeled antibody or antibody fragment is fluorescently labeled.

The outcome of step (ii) is a sample S in which the Vim3 in the spermatozoa is stained, preferably by a dye (in particular a fluorescence dye) or a metal label (in particular a (colloidal) gold label), in particular a fluorescently labeled antibody.

Alternatively, detection of a bound Vim3-specific antibody or antibody fragment (optionally unlabeled) may be also conducted by any other method known in the art such as e.g., surface plasmon resonance (SPR) or related methods.

In a preferred embodiment of the present invention, the presence or absence of Vim3 is detected by detecting Vim3 protein expression in the sample and/or localization of Vim3 in the spermatozoa. General protein detection methods in the art which are suitable for methods of rapid diagnosis of ejaculates from patients which are in the position to conceive children are immuno-electrophoresis, immuno-blotting, Western blot, SDS-PAGE, capillary electrophoresis (CE), spectrophotometry or enzyme assay for example, and dipsticks (lateral flow) but not limited to these.

Preferably, detecting (step (iii)) is an imaging step, more preferably a microscopic step, in particular a fluorescence microscopic step. Exemplarily, fluorescence microscopy may comprise one or more of the following methods: laser scanning microscopy (LSM), two-photon fluorescence microscopy, fluorescence molecular imaging (FMI), fluorescence energy transfer (FRET), fluorescence correlation spectroscopy (FCS), and/or fluorescence cross-correlation spectroscopy (FCCS). All these techniques as such are well-known to those skilled in the art. In the imaging step, the Vim3 in the spermatozoa may fluorescently stained by a fluorescently labeled antibody (e.g., as exemplified herein), the excess fluorescently labeled antibody is washed away and the Vim3 localization and intensity is determined in a number of spermatozoa. Typically, a diminished fluorescence signal per spermatozoon, more preferably in the mid piece, more in particular the neck region, of the spermatozoa contained in the sample S in comparison to the control sample C+ indicates decreased fertility of the spermatozoa contained in the sample S. This is further exemplified in the example section. This also applies to the detection of a signal per spermatozoon comparable to control sample C−.

Alternatively or additionally, detecting (step (iii)) may be performed by flow cytometry. Accordingly, in a preferred embodiment, step (ii) of staining intracellular Vim3 is staining with a fluorescently labeled marker and wherein the step (iii) is detecting the total content of the Vim3 per spermatozoon conducted by means of flow cytometry.

Preferably, the spermatozoa are stained by a Vim3-specific antibody or antibody fragment and populations of higher and lower fluorescence intensity are distinguished from another (e.g., as exemplified herein), the excess fluorescently labeled antibody may be washed away and the Vim3 per cell may be determined by flow cytometry. Typically, a diminished fluorescence signal per spermatozoon in comparison to the control sample C+ indicates decreased fertility of the spermatozoa contained in the sample S. This also applies to the detection of a signal per spermatozoon comparable to control sample C−. This is further exemplified in the example section. Optionally, the threshold between these two groups may be adjusted by setting the flow cytometer (FACS) by a positive sample S+ containing spermatozoa of high fertility (=high fluorescence) and a negative sample S− containing spermatozoa of low fertility (=low fluorescence). The negative sample S− may optionally also be a sample of another species lacking Vim3 of the species of interest and thus not bound by the Vim3-specific antibody or antibody fragment.

Alternatively or additionally, detecting (step (iii)) may be performed by Western blot or ELISA (enzyme linked immunosorbent assay). These techniques which are well-known by those in the art may provide information on the total amount of Vim3 expressed in the spermatozoa in the investigated sample S. Typically, a diminished amount of Vim3 per spermatozoon in comparison to the control sample C+ indicates decreased fertility of the spermatozoa contained in the sample S. This also applies to the detection of a signal per spermatozoon comparable to control sample C−.

Optionally, Vim3 may be concentrated in the sample S prior to being analyzed further. Exemplarily, beads coated with a Vim3-specific antibody or antibody fragment may be used to obtain higher amounts of Vim3 from the sample S. For this purpose, exemplarily agarose beads may be used, in particular agarose beads bearing an antibody-binding entity such as, e.g., protein A. It will be understood that also any other kinds of beads usable from this purpose may be used in this context such as, exemplarily, silica or magnetic beads. Also the conjugation method may be freely chosen. Exemplarily, a biotin-conjugated Vim3-specific antibody or antibody fragment may be immobilized on a streptavidin-bearing bead or a bead bearing maleinimidyl groups may be contacted with a cysteinyl-bearing Vim3-specific antibody or antibody fragment or the bead may bear amino group-binding residues such as succinimidyl esters. In any case, such bead may then be conjugated with a Vim3-specific antibody or antibody fragment. After washing the beads, the beads coated with a Vim3-specific antibody or antibody fragment may be contacted with the sample S and incubated in order to allow the binding of the antibody to its molecular target Vim3. Then, the beads may be removed from the liquid sample S (e.g., by means of centrifugation, filtration, crossflow filtration, or the like, or, in case of using magnetic beads, by means of magnetic forces) and may be optionally washed with a buffer. The Vim3 may then be cleaved off and investigated further such as e.g., by means of Western blot, flow cytometry, or any other method described herein, or a combination of two or more of these methods. If a defined amount of beads coated with a Vim3-specific antibody or antibody fragment and a defined amount of sample S is used, this procedure may provide (semi-)quantitative results by comparing the amount of Vim3 in the sample S with the sample S+.

Optionally, such beads coated with a Vim3-specific antibody or antibody fragment may also be labelled by itself (e.g., by means of a dye (e.g., a fluorescence dye) or a metal label (e.g., gold beads)).

Optionally, such beads coated with a Vim3-specific antibody or antibody fragment which have been bound to Vim3 may also be subjected to a labeled Vim3-specific antibody or antibody fragment. Then, the intensity of label per bead may be detected such as, e.g., by means of flow cytometry. Also this may provide (semi-) quantitative results by comparing the amount of Vim3 in the sample S with the sample S+.

Alternative to a bead, also other means for concentrating the Vim3 in the sample may be used such as, e.g., affinity chromatography (e.g., with a solid phase based on beads or a monolithic structure).

Alternatively or additionally, detecting (step (iii)) may be performed by means of lateral flow (e.g., dipstick) analysis. Such dipstick usable in the context of the present invention preferably comprises a Vim3-specific antibody or antibody fragment. Examples for such dipsticks are provided in detail herein. When using a dipstick for conducting the method of the present invention means that the sample S is typically liquid, semi-liquid or liquefied so that it can be soaked by a carrier of the dipstick. Typically, the sample S comprises an aqueous liquid. Exemplarily, the sample S usable by the dipstick analysis may be a semen sample. A dipstick can be a fast and reliable result of man fertility.

Alternatively or additionally, detecting and determining steps (steps (iii) and (iv)) may also be conducted by polymerase chain reaction (PCR) as described in WO 2014/154686. Then, preferably, Vim3 specific primers as described in WO 2014/154686 are used. Such PCR may provide information on the integrity of the Vim3 gene in the spermatozoa and indirectly provide information on the total content of Vim3 per spermatozoon. Alternatively or additionally, real time PCR (RT-PCR), may provide information on the expression of Vim3 in an ejaculate sample.

Optionally, the above methods may comprise statistical procedures to assess whether two values are significantly different from each other such as Student's t-test or chi-square test. The control value or background value may be obtained by carrying out the method of the present invention additionally and simultaneously with one or more controls (e.g., a sample of low fertility C−), a background or blank sample (C0). Alternatively, it may be a value determined previously, e.g. a value provided by a third person, e.g. the manufacturer of laboratory equipment or a published value known from the art. As described above, a control sample C+ representing normozoospermia is typically used. This also applies to the detection of a signal per spermatozoon comparable to control sample C−.

The readout may be performed manually or via a computer-assisted automated manner. Likewise, the analysis of the determined accumulation may be performed manually or via a computer-assisted automated manner.

In a preferred embodiment, steps (iv) and (v) are performed by a computer-assisted automated manner.

Additionally, the method may optionally also be combined with one or more classical means for determining the fertility of spermatozoa, such as light microscopic analysis (spermiogram) of spermatozoa movability and/or morphology.

In a preferred embodiment, the method of the present invention is combined with the further step
(vi) comparing the microscopic movability and/or morphology appearance of the spermatozoa between the sample S and
   (a) at least one control sample C+ of spermatozoa of high fertility of the same species, and/or
   (b) at least one control sample C− of spermatozoa of low fertility of the same species,
wherein a decreased amount of movability and/or a deviation in morphology of the spermatozoa in the sample S indicates decreased fertility of the spermatozoa contained in the sample S.

This optional step (vi) may be performed in a separate aliquot of in the same aliquot as steps (i)-(v) of the method of the present invention. Preferably, step (vi) is performed in a separate aliquot.

When step (vi) is performed in a separate aliquot, step (vi) may optionally be performed before, simultaneous or subsequent to the steps (i)-(v) of the method of the present invention. Performing step (vi) in a separate aliquot may bear the advantage that the staining (step (ii)) does not interfere and using toxic agents for staining, including fixation of the spermatozoa, are not excluded from the method.

When step (vi) is performed in the same aliquot of sample S, step (vi) may optionally be performed before steps (i)-(v) of the method of the present invention or it may be performed simultaneously with steps (iv) and (v) or it may be performed subsequent to steps (i)-(v) of the method of the present invention. When step (vi) is performed before steps (i)-(v) of the method of the present invention, then it may be performed with unstained spermatozoa.

The sample S may be an fixed specimen. However, preferably, the sample S comprises viable spermatozoa still suitable of sexual reproduction.

Accordingly, in a preferred embodiment, the sample S is of interest for sexual reproduction of a human or non-human animal, preferably wherein the sample S is or is derived from an ejaculate of a male human or male non-human animal.

When the sample S is an ejaculate, it may be immediately be obtained from the male human or male non-human animal or may be stored under suitable conditions maintaining viability (e.g., by means of shock-freezing (e.g., in liquid nitrogen)). A non-human animal preferably is a non-human mammal (e.g., a domestic mammal (e.g., a bovine, a pig, a horse, a donkey, a sheep, a camel, a goat, a dog, a cat, etc.) or another mammal intended for propagation (e.g., an endangered species (e.g., a tiger, an elephant, etc.)).

A sample S derived from an ejaculate may be an ejaculate or aliquot thereof that may optionally be diluted in a liquid maintain the viability of the viability of the spermatozoa (e.g., by means of an aqueous buffer and/or an organic solvent (e.g., dimethyl sulfoxide)). It will be understood that also such sample S derived from an ejaculate may optionally be stored under suitable conditions maintaining viability (e.g., by means of shock-freezing (e.g., in liquid nitrogen)).

The method of the present invention may have particular benefit on improving the sexual reproduction of humans and non-human animals.

Accordingly, in a preferred embodiment, the sample S is a male human or male non-human animal sperm donation of interest for artificial insemination.

In human reproductive medicine, the fertility of man is an interesting factor for achieving pregnancy. On the one hand couples facing undesired childlessness are interested in determining any hindsight of why pregnancy is not achieved. Not least, the male sterility that is often associated with a comparably low level of spermatozoa fertility is of interest. In this context, the method of the present invention may provide information. From the finding of being aware of a comparably low level of spermatozoa fertility, suitable treatments may be considered.

Often, spermatozoa fertility is diminished to such degree that it is considered as a pathologic condition. As used herein, a pathologic condition may be understood in the broadest sense as any health state deviating from healthy state. Depending on the severity of the pathologic condition, it may also be designated as disease, illness, malady or the like.

Accordingly, in a preferred embodiment, the decreased fertility of the spermatozoa contained in the sample S is associated with at least one pathologic condition of the donor of the spermatozoa contained in the sample S according to at least one of classes N46 and R86 of the $10^{th}$ revision of the International Statistical Classification of Diseases and Related Health Problems of the World Health Organization in the version of 2016 (ICD-10).

In a more preferred embodiment, decreased amount of accumulation of Vim3 in the mid piece, more in particular the neck region, of the spermatozoa contained in the sample S in comparison to the control sample C+ and/or a decreased amount of the total content of Vim3 per spermatozoon contained in the sample S in comparison to the control sample C+ indicates at least one pathologic condition selected from the group consisting of oligozoospermia, asthenozoospermia and teratozoospermia.

In another highly preferred embodiment, a decreased amount of accumulation of Vim3 in the mid piece, more in particular the neck region, of the spermatozoa indicates oligo-astheno-teratozoospermia (OAT syndrome).

Furthermore, also a sperm donation of a donor of unknown fertility, in particular a sperm donation comprised in a sperm bank, may be tested by the method of the present invention in order to access fertility thereof. This may avoid using per se infertile sperm donations for artificial insemination. Optionally, a portion A comprising spermatozoa of high fertility may be selected from such sperm bank.

On the other hand, for agricultural use as well as for wildlife conservation programs, high reproduction rates may be desired. In this context, it is desired to select male animals of particularly high fertility and, optionally, breed those further. Today, for many farm animals mostly artificial insemination is used for breeding, such as e.g., for bovines. A sperm donation of a donor animal of unknown fertility, in particular a sperm donation comprised in a sperm bank, may be tested by the method of the present invention in order to access fertility thereof. This may avoid using per se infertile sperm donations for artificial insemination. Optionally, a portion A comprising spermatozoa of high fertility may be selected from such sperm bank.

In a particularly preferred embodiment, the method of the present invention comprises the following steps:
  (i) providing an aliquot of the sample S containing spermatozoa of interest for sexual reproduction of a human or non-human animal, preferably wherein the sample S is or is derived from an ejaculate of a male human or male non-human animal;
  (ii) optionally staining intracellular Vim3 the spermatozoa with a fluorescently labeled marker, in particular by binding of AB1-L or a combination of AB1-ul and AB2-L;
  (iii) detecting the localization of the Vim3 within the stained spermatozoa, wherein the Vim3 is optionally stained Vim3 of step (ii), by fluorescence microscopy;
  (iv) determining the degree of accumulation of Vim3 in the mid piece, more in particular the neck region, of the spermatozoa; and
  (v) comparing the degree of accumulation of Vim3 determined in step (iv) between the sample S and
    (a) at least one control sample C+ of spermatozoa of high fertility of the same species, and/or
    (b) at least one control sample C− of spermatozoa of low fertility of the same species,
wherein a decreased amount of accumulation of Vim3 in the mid piece, more in particular the neck region, of the spermatozoa in the sample S as determined in step (v) indicates decreased fertility of the spermatozoa contained in the sample S.

In an alternative highly preferred embodiment, the method of the present invention comprises the following steps:
  (i) providing an aliquot of the sample S containing spermatozoa of interest for sexual reproduction of a human or non-human animal, preferably wherein the sample S is or is derived from an ejaculate of a male human or male non-human animal;
  (ii) optionally staining intracellular Vim3 the spermatozoa with a fluorescently labeled marker, in particular by binding of AB1-L or a combination of AB1-ul and AB2-L;
  (iii) detecting the total content of the Vim3 per spermatozoon, wherein the Vim3 is optionally stained Vim3 of step (ii), in particular by flow cytometry and/or ELISA;
  (iv) determining the total content of Vim3 per spermatozoon; and
  (v) comparing the total content of Vim3 per spermatozoon determined in step (iv) between the sample S and
    (a) at least one control sample C+ of spermatozoa of high fertility of the same species, and/or
    (b) at least one control sample C− of spermatozoa of low fertility of the same species,
wherein a decreased amount of the total content of Vim3 per spermatozoon contained in the sample S in comparison to the control sample C+; and/or an amount of the total content of Vim3 per spermatozoon contained in the sample S that is not higher than in the control sample C−;
indicates decreased fertility of the spermatozoa contained in the sample S.

In an alternative particularly preferred embodiment, the method of the present invention comprises the following steps:
  (i) providing an aliquot of the sample S containing spermatozoa of interest for sexual reproduction of a human or non-human animal, preferably wherein the sample S is or is derived from an ejaculate of a male human or male non-human animal;
  (ii) optionally staining intracellular Vim3 the spermatozoa with a fluorescence labeled marker, in particular by binding of AB1-L or a combination of AB1-ul and AB2-L;
  (iii) detecting the spatial localization of the Vim3 within the stained spermatozoa, wherein the Vim3 is optionally stained Vim3 of step (ii), by fluorescence microscopy and/or total content of the Vim3 per spermatozoon, wherein the Vim3 is optionally stained Vim3 of step (ii), in particular by flow cytometry and/or ELISA;
  (iv) determining the degree of accumulation of Vim3 in the mid piece, more in particular the neck region of the spermatozoa, and/or the total content of Vim3 per spermatozoon; and
  (v) comparing the degree of accumulation of Vim3 and/or the total content of Vim3 per spermatozoon determined in step (iv) between the sample S and
    (a) at least one control sample C+ of spermatozoa of high fertility of the same species, and/or
    (b) at least one control sample C− of spermatozoa of low fertility of the same species,
wherein
  a decreased amount of the total content of Vim3 per spermatozoon contained in the sample S in comparison to the control sample C+;
  an amount of the total content of Vim3 per spermatozoon contained in the sample S that is not higher than in the control sample C−;
  a decreased amount of accumulation of Vim3 in the mid piece, more in particular the neck region, of the spermatozoa contained in the sample S in comparison to the control sample C+; and/or
  an amount of accumulation of Vim3 in the mid piece, more in particular the neck region, of the spermatozoa contained in the sample S that is not higher than in the control sample C−,
indicates decreased fertility of the spermatozoa contained in the sample S.

Optionally, the method of the present invention may also be supported by additional steps.

In a preferred embodiment, the method further comprises the additional step:
  (vi) comparing the microscopic movability and/or morphology appearance of the spermatozoa between the sample S and
    (a) at least one control sample C+ of spermatozoa of high fertility of the same species, and/or
    (b) at least one control sample C− of spermatozoa of low fertility of the same species,
wherein a decreased amount of movability of the spermatozoa and/or a deviation in morphology of the spermatozoa in the sample S as determined in step (vi) in combination with a decreased amount of accumulation of Vim3 in the mid piece of the spermatozoa and/or a decreased amount of the total content of Vim3 per spermatozoon in the sample S as determined in step (v), indicates decreased fertility of the spermatozoa contained in the sample S.

The method may optionally further comprise the step of treating a patient whose spermatozoa have been found to bear decreased fertility. Additionally or alternatively, the method may optionally further comprise the step of artificial insemination or in vitro fertilization with the spermatozoa of a patient whose spermatozoa have been found to bear decreased fertility.

Another aspect of the present invention relates to the use of Vim3 as a marker for fertility of spermatozoa, wherein a decreased amount of the total content of Vim3 per spermatozoon and/or a decreased amount of accumulation of Vim3 in the mid piece of the spermatozoa indicates decreased fertility of the spermatozoa.

Preferably, this use comprises one or more of the method steps as laid out above, in particular is conducted according to a method of the present invention as laid out herein. It will be understood that the specifications made in the context of the method as such as described above apply *mutatis mutandis* to the use.

As indicated above, the method of the present invention is a method that may also be used in a medicinal and diagnostic context.

Accordingly, a further aspect of the present invention relates to a Vim3-specific antibody or antibody fragment for use in a method of diagnosing a pathologic condition associated with decreased fertility in a patient, wherein said method is conducted according to the present invention, wherein the sample S is a semen sample obtained from the patient, and wherein the pathologic condition associated with decreased fertility preferably is a pathologic condition according to at least one of classes N46 and R86 of the ICD-10.

It will be understood that the specifications made in the context of the method as such as described above apply *mutatis mutandis* to the Vim3-specific antibody or antibody fragment for use.

In a preferred embodiment, the pathologic condition is selected from the group consisting of oligozoospermia, asthenozoospermia and teratozoospermia.

In another highly preferred embodiment, the pathologic condition is oligo-astheno-teratozoospermia (OAT syndrome).

As indicated above, the methods and uses of the present invention can also be conducted by means of a dipstick analysis (lateral flow analysis).

Accordingly, a further aspect of the present invention relates to a dipstick (preferably usable for the method of or the use of the present invention) comprising, placed in the direction of flow of the sample S, on a carrier that is suitable for soaking the sample S, the following:
- (0) an edge or segment suitible for soaking the sample S;
- (1) optionally a stripe (1) comprising labeled Vim3-specific antibodies or antibody fragments which are not immobilized and freely movable when the sample S passes through this stripe (1);
- (2) a stripe (2) comprising immobilized unlabeled vimentin-specific, in particular Vim3-specific, antibodies or antibody fragments; and
- (3) optionally a stripe (3) of immobilized unlabeled antibodies or antibody fragments specifically binding the labeled Vim3-specific antibodies or antibody fragments of stripe (1).

Accordingly, a dipstick according to the present invention (preferably usable for the method of or the use of the present invention) comprise at least, placed in the direction of flow of the sample S, on a carrier that is suitable for soaking the sample S, the following:
- (0) an edge or segment suitible for soaking the sample S; and
- (2) a stripe (2) comprising immobilized unlabeled vimentin-specific, in particular Vim3-specific, antibodies or antibody fragments.

Examples for setups is provided in FIGS. 5 and 6 herein.

As used herein, the terms "dipstick", "dip-stick", "test strip", "control strip", "diagnostic/medical dipstick" may be understood interchangeably in the broadest sense as any device that is usable to test a sample S in the context of the present invention (according to the lateral flow technique).

In the context of the dipstick, the sample S is typically liquid, semi-liquid or liquefied so that it can be soaked by a carrier of the dipstick. Typically, the sample S comprises an aqueous liquid. Exemplarily, the sample S usable by the dipstick may be a semen sample (e.g., ejaculate).

In particular if the dipstick lacks stripe (1), the sample S is preferably premixed with a labeled Vim3-specific antibody or antibody fragment. The volume and molar ratios will be adapted accordingly in order to optimize binding efficiency.

The volume of the sample S (optionally diluted and/or premixed with a labeled Vim3-specific antibody or antibody fragment) added to the dipstick will be adapted to the size and material of the dipstick. Typical volumes for adding to a segment suitable for soaking the sample S are in the range of from 10 to 1000 µl, preferably 50 to 500 µl, in particular 75 to 300 µl, exemplarily (approximately 200 µl).

Exemplarily, the carrier may be a (hydro) gel or a piece of paper board, and may be optionally film laminated. Typically, the dipstick will be stored in dry state and is moistened by the sample S. When conducting the method of the present invention by means of the dipstick, the edge or segment suitable for soaking the sample S (0) may be contacted with the sample S. This is preferably conducted long enough to enable the sample liquid to be soaked in the carrier of the dipstick. The other parts of the dipstick are preferably not directly contacted with the sample S.

It is preferably enabled that the sample S flows through the carrier of the dipstick at least until the stripes (1) (if present) and (2) and optionally (3) have been passed by the sample S or parts thereof.

According to a preferred embodiment, the sample S is of a first species and the antibodies or antibody fragments of each of stripe (1) (if present) or the antibodies or fragments used for premixing with the sample S (in particular if stripe (1) is not present) on the one hand and (2) and optionally (3) of the other hand are each of different species.

In a preferred embodiment, the immobilized unlabeled antibodies or antibody fragments of stripe (3) specifically bind to the Fc fragment of the labeled Vim3-specific antibodies or antibody fragments of stripe (1) (if present) or premixed with the spermatozoa in solution (in particular if stripe (1) is not present). Exemplarily, the Vim3-specific antibodies or antibody fragments which are not immobilized are (preferably monoclonal) rabbit antibodies. Then, the immobilized antibodies of stripe (3) may be (preferably monoclonal) antibodies directed against the Fc part of the antibodies provided in stripe (1) or premixed with the spermatozoa in solution (in particular if stripe (1) is not present).

The label may be a fluorescence label, a visible dye label or, particularly preferably, a (colloidal) gold label. Such (colloidal) gold may be added to an antibody or antibody fragment bay any means, exemplarily by means of a GOLD Conjugation Kit.

When a Vim3-containg sample (S+) is added to the dipstick, upon flowing through the dipstick, the labeled Vim3-specific antibodies may bind to Vim3 in the spermatozoa and form a spematoza: Vim3-specific antibody conjugate. This conjugate will then binding to the unlabeled Vim3-specific antibodies of stripe.

When a sample lacking Vim3 (S−) is added to the dipstick, upon flowing through the dipstick, the labeled Vim3-specific antibodies will not form a spematoza:Vim3-specific antibody conjugate. Therefore, the spermatozoa comprised in the sample S will then pass by the stripe (2) without being bound and will pass through the dipstick until the stripe (3).

In such dipstick, the ratio between signal intensity of the label in stripe (2) and (3) indicates fertility. A higher (2):(3) ratio indicates higher fertility, whereas a lower (2):(3) ratio indicates lower fertility in the sense of the method of the present invention laid out above.

In a preferred embodiment, the dipstick (preferably usable for the method of or the use of the present invention) comprises, placed in the direction of flow of the sample S, on a carrier that is suitable for soaking the sample S, the following:
- (0) an edge or segment suitable for soaking the sample S;
- (1) a stripe (1) comprising labeled Vim3-specific antibodies or antibody fragments which are not immobilized and freely movable when the sample S passes through this stripe (1);
- (2) a stripe (2) comprising immobilized unlabeled Vim3-specific antibodies or antibody fragments; and
- (3) optionally a stripe (3) of immobilized unlabeled antibodies or antibody fragments specifically binding the labeled Vim3-specific antibodies or antibody fragments of stripe (1).

In an alternative preferred embodiment, the dipstick (preferably usable for the method of or the use of the present invention) comprises, placed in the direction of flow of the sample S premixed with labeled Vim3-specific antibodies or antibody fragments (which are not immobilized and freely movable) on a carrier that is suitable for soaking the sample S premixed with labeled Vim3-specific antibodies or antibody fragments, the following:
- (0) an edge or segment suitable for soaking the sample S premixed with labeled Vim3-specific antibodies or antibody fragments;
- (2) a stripe (2) comprising immobilized unlabeled vimentin-specific (either directed against vimentin in general or Vim3-specific) antibodies or antibody fragments; and
- (3) optionally a stripe (3) of immobilized unlabeled antibodies or antibody fragments specifically binding the labeled Vim3-specific antibodies or antibody fragments of stripe (1).

In a preferred embodiment, the vimentin-specific antibody used in stripe (2) is directed to both forms (e.g., 3B4 and SP20). The premixing of the labeled Vim3-specific antibodies or antibody fragments may be followed by an incubation to allow and optimize binding of the Vim3-specific antibodies or antibody fragments to its molecular target Vim3. This may exemplarily be performed by incubating for 10 to 60 min at a temperature of from 2 to 25° C.

Alternatively or additionally, a dipstick according to the present invention may be may be prepared according to Preechakasedkit et al., 2012, Biosens Bioelectron 31(1):562-566; Tao et al., 2014, Lett Appl Microbiol 59(2):247-251 or Wang et al., 2010, J Virol Methods 2010, 170(1-2):80-85.

As indicated above, the method of the present invention also enable the selective choice of a portion A comprising spermatozoa of high fertility, e.g., from a sperm bank comprising a variety of human and non-human ejaculate aliquots.

Accordingly, a further aspect of the present invention relates to a method for obtaining a portion A sufficient for sexual reproduction of a human or non-human animal containing spermatozoa of high fertility, said method comprising the following steps:

(1) providing one or more samples S containing spermatozoa potentially suitable for sexual reproduction;
(2) determining the fertility of the sample S of step (1) by means of the method of the present invention;
(3) classifying the fertility of the sample S determined by step (2) as:
  (A) a sample S+ containing spermatozoa of high fertility, or
  (B) a sample S− containing spermatozoa of low fertility,
  by setting a threshold value between (a) a first control sample C+ of spermatozoa of high fertility and (b) a second control sample C− of spermatozoa of low fertility, wherein C+ and C− are of the same species as sample S;
(4) selecting and obtaining a sample S+ containing spermatozoa of higher fertility above the threshold fertility according to step (3) as portion A.

It will be understood that the specifications made in the context of the method as such as described above apply *mutatis mutandis* to such method for obtaining a portion A sufficient for sexual reproduction.

In a preferred embodiment, the portion A is or is derived from a sperm donation of interest for artificial insemination obtained from a male human or a male non-human animal.

As indicated above, this may be particularly beneficial for improving the selection of sperm donations, e.g., from a sperm bank. This is often particularly desired for breeding non-human animals, e.g., for agricultural use.

Accordingly, in a particularly preferred embodiment, the portion A is or is derived from a sperm donation of interest for artificial insemination obtained from a male non-human animal which is a mammal intended for breeding.

Accordingly, such method may also be employed for selecting and breeding animals of high fertility.

Accordingly, a still further aspect of the present invention relates to a method for obtaining a non-human male animal bearing spermatozoa of high fertility, said method comprising the steps:

(I) providing a variety of samples S containing spermatozoa potentially suitable for sexual reproduction, in particular wherein said samples S are derived from ejaculates obtained from non-human male animals each of the same species SP;
(II) determining the fertility of the samples S of step (I) by means of the method of the present invention;
(III) identifying a sample S+ of high fertility suitable for sexual reproduction based on the findings of step (II);
(IV) inseminating a non-human female animal of species SP susceptible for pregnancy with the selected sample S+ as identified in step (III) by means of artificial insemination or copulation with the male non-human animal from which sample S+ has been derived from; and
(V) enabling the gestation of the progeny obtained from step (IV) in the female animal, subsequent birth and obtaining the non-human male animal of high fertility.

It will be understood that the specifications made in the context of the method as such as described above apply *mutatis mutandis* to such method for obtaining a non-human male animal bearing spermatozoa of high fertility.

It will be noted that this method is in principle employable independent on the species of the animal as long as the animal spermatozoa express Vim3. In particular, the method is independent on the race of the animal.

The present invention also relates to a test kit comprising one or more reagents useful for practicing the method according to the present invention. A kit generally includes a package with one or more containers holding the reagents, as one or more separate compositions or, optionally, as a mixture if reagents are compatible. The kit may also include other material(s), which may be desirable from a user standpoint, such as a buffer(s), a diluent(s), a standard(s), and/or any other material useful in sample processing, washing, or conducting any other step of the assay. A kit according to the present invention may include a solid phase and a capture agent affixed to the solid phase, wherein the capture agent is an antibody specific for the analysis (e.g., a Vim3-specific antibody) being assessed in the test sample. The solid phase may comprise a material such as a magnetic or paramagnetic particle including a microparticle, a bead, a test tube, a microtiter plate, a cuvette, a membrane, a scaffolding molecule, a quartz crystal, a film, a filter paper, a dipstick a disc or a chip.

A Test kit according to the present invention may preferably further comprise user instructions for carrying out one or more of the methods of the invention.

Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, for example, computer media including, but are not limited to, electronic storage media (e.g., magnetic discs, tapes, cartridges, chips), optical media (e.g., CD ROM), and the like.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a", "an", and "the" include plural reference unless the context clearly dictates otherwise. Similarly, the words "comprise", "contain", "include" and "encompass" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, some exemplified preferred methods and materials are described herein.

The following Examples as well as the accompanying Figures are intended to provide illustrative embodiments of the present invention described and claimed herein. These Examples and Figures are not intended to provide any limitation on the scope of the invented subject-matter.

BRIEF DESCRIPTION OF THE FIGURES

FIG. 1 shows the intracellular localization of fluorescently labeled Vim3 in the spermatozoa at a magnification of ×10.

FIG. 2 shows the intracellular localization of fluorescently labeled Vim3 in the spermatozoa at a magnification of ×100.

FIG. 3 shows the calculation of Vim3 positive sperms. The fluorescence was at the same intensity for both. The normozoospermia was used as "standard" intensity. Five different samples of each group were calculated and always 100 sperms were counted. The result is statistical significant $p<0.001$.

FIG. 5A shows the dipstick before use. Herein, (1) indicates a stripe comprising labeled Vim3-specific antibodies (depicted as stars), which are not immobilized and freely movable when the sample S passes through this stripe. (2) indicates a stripe comprising immobilized unlabeled Vim3-specific antibodies. (3) indicates a stripe of immobilized unlabeled antibodies specifically binding the labeled Vim3-specific antibodies (depicted as stars). S indicates the sample S to be added to the dipstick. (4) indicates the flow direction of the moisten sample S. FIG. 5b shows the results when a Vim3-containing sample (S+) is added to the dipstick. Then, upon flowing through the dipstick (4), the labeled Vim3-specific antibodies are binding to Vim3 in the spermatozoa and form a spematoza:Vim3-specific antibody conjugate. This conjugate is then binding to the unlabeled Vim3-specific antibodies of stripe (2). FIG. 5c shows the results when a sample lacking Vim3 (S−) is added to the dipstick. Then, upon flowing through the dipstick (4), the labeled Vim3-specific antibodies are not bound until the stripe (3). Thus, the ratio between signal intensity of the label in stripe (2) and (3) indicates fertility. A higher (2):(3) ratio indicates higher fertility, whereas a lower (2):(3) ratio indicates lower fertility.

FIG. 6A shows the dipstick before use. Herein, the sample S (e.g. ejaculate) is premixed with a labeled Vim3-specific antibodies (depicted as stars). (2) indicates a stripe comprising immobilized unlabeled vimentin-specific antibodies. (3) indicates a stripe of immobilized unlabeled antibodies specifically binding the labeled Vim3-specific antibodies (depicted as stars). (4) indicates the flow direction of the moisten sample S. FIG. 6b shows the results when a Vim3-contaning sample (S+) premixed with a labeled Vim3-specific antibodies (depicted as stars) is added to the dipstick. Then, the a labeled Vim3-specific antibodies (depicted as stars) and the Vim3 in the spermatozoa form a spematoza:Vim3-specific antibody conjugate. After adding this sample to the dipstick, it flows through the dipstick (4). The spematoza:Vim3-specific antibody conjugate is then binding to the unlabeled Vim3-specific antibodies of stripe (2). FIG. 6c shows the results when a sample lacking Vim3 (S−) premixed with a labeled Vim3-specific antibodies (depicted as stars) is added to the dipstick. Then, the labeled Vim3-specific antibodies (depicted as stars) are not binding to the spermatozoa. Thus, upon flowing through the dipstick (4), the labeled Vim3-specific antibodies are not bound until the stripe (3). Thus, the ratio between signal intensity of the label in stripe (2) and (3) indicates fertility. A higher (2):(3) ratio indicates higher fertility, whereas a lower (2):(3) ratio indicates lower fertility.

EXAMPLES

Figure 1A:
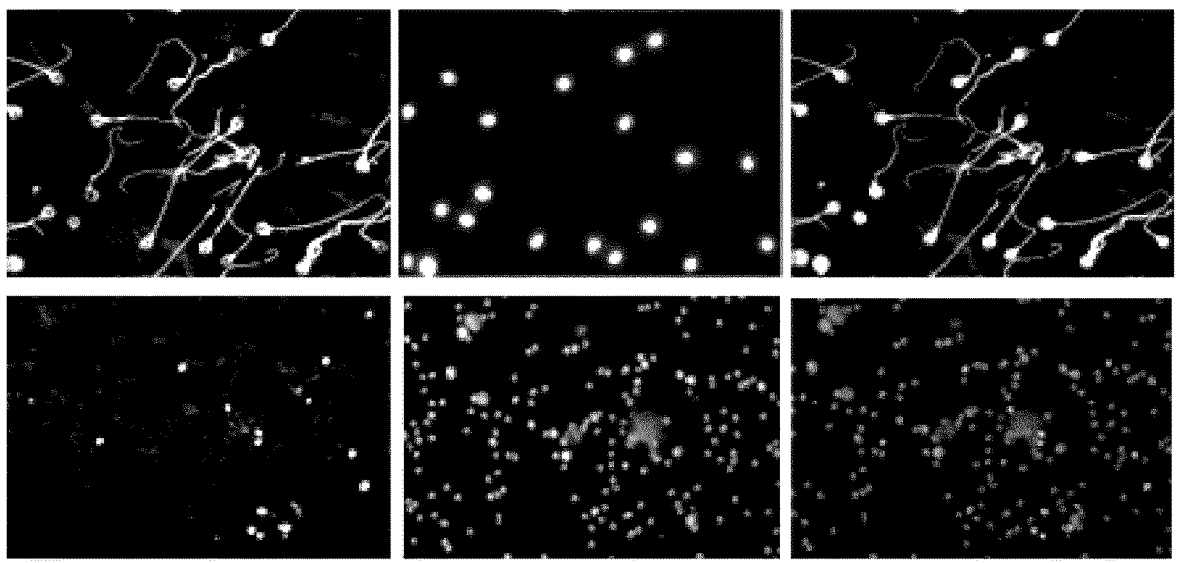
FIG. 1A: Immunofluorescence showing expression of Vim3 (upper left image) in normozoospermia. The staining of the sperm head (DAPI stain) is depicted in the images in the middle (upper middle and lower middle. The right images depict the overlay of the aforementioned (upper right and lower right). Localization of the Vim3 predominantly located in the neck and tail region. The Vimentin full length (V9) (lower left) shows a dominant location in the head region.

Vimentin 3 the New Marker for Fertility Proof

Materials and Methods

Antibody Design and Quantification

The Vim3 antibody was commercially designed (Davids Biotechnologie GmbH), using the last 8 amino acids (RGKHFISL: SEQ ID No: 2) of the unique C-terminal ending of Vim3 as target. Its expression versus that of full length Vimentin V9 (sc-6260; Santa Cruz, Heidelberg) was analyzed using ejaculate probes from patients which came into our outpatient clinic with the question of fertility. Western blot analysis of macro-dissected material of cryptal epithelial cells and lymphoid cells was performed for further evaluation and proof of specificity of the newly designed antibody.

Ejaculates

The ejaculates were collected from patients and analyzed according to the WHO reforms. After categorization of the ejaculates, they were either frozen at −20° C. or immediately analyzed.

Immune Histology of Testicular Human Biopsy Samples

Paraffin-embedded tissue sections (4 μm thick) were deparaffinized by incubation for 2-5 minutes in xylene, followed by 2-3 minutes in 100% ethanol, and 1 minute in 95% ethanol; and then rinsed with distilled water. The slides were incubated with a specific serum blocker (anti-rabbit) for 30 minutes to avoid unspecific binding. After that incubation period, the slides were re-incubated for 1 hour at room temperature with specific primary antibodies (Vimentin 3, EZBiolab, Inc. Carmel, USA or Vimentin V9, sc-6260, Santa Cruz, Heidelberg, Germany). After washes with PBS-Tween 20 (Phosphate Buffered Saline), sections were incubated with a secondary anti-rabbit antibody (Santa Cruz, Heidelberg, Germany). After rinsing with PBS-Tween 20, slides were re-incubated for 2 minutes in 95% ethanol, followed by 2-3 minutes in 100% methanol, counterstained with H&E (Hematoxylin and Eosin), and cover-slipped.

Immunofluorescence

Ejaculates were mixed, 100 μl were centrifuged at 2500×g and the supernatant was discarded. The pellet was washed 2× with 500 μl 1×PBS and centrifuged at 2500×g. After washing, the pellet was diluted in 50 μl 1×PBS and 10 μl were spread on special coated slides. The slide was incubated at 37° C. for 1 hour and washed under fluent water. The Vim3 or Vimentin V9 antibody was diluted in 1×PBS and used in a concentration of 1:200, the incubation was performed at 37° C. for 1 hour. After primary antibody incubation, the slides were washed 3× in 1×PBS and the second antibody (either FITC anti-rabbit or Alexa 594 anti-rabbit) was incubated for 30 min and washed 2× with 1×PBS. Finally the slides were covered with DAPI mounting medium and analyzed with the Fluorescence microscope DP7. For analysis and evaluation the Diskus software was used.

Statistics

For statistical analysis between normozoospermia and OAT syndrome patients, ejaculates from 5 different donors per group were collected and stained with Vim3. For statistical analysis between normozoospermia and teratozoospermia patients, ejaculates from 4 different donors per group were collected and stained with Vim3. The intensity of sperms from normozoospermia patients were used as standard. From each samples 100 sperms were counted. For statistical analysis the GraphPrism 5 program was used. Analysis of variance (ANOVA) was performed and the significant differences were calculated ($*p<0.05, p<0.01, *p<0.001$).

Flow Cytometry

100 μl of each ejaculate was washed as described above with 1×PBS. Cell Fixation and Cell permeabilization kit (Thermo Scientific) was used according to the manufactures protocol. The incubation with the Vim3 antibody was performed for 1 hour at room temperature; sperms were washed with PBS twice and incubated with a secondary Alexa 488 antibody for 20 mins. As control 293t cells were used to proof the signal intensity. The appropriated controls were performed.

Flow cytometry was performed by FACSCanto I (Becton Dickinson) and obtained data was analyzed using FlowJo (Tree Star).

Results

Vimentin 3 Expression in Sperms

Figure 1B:
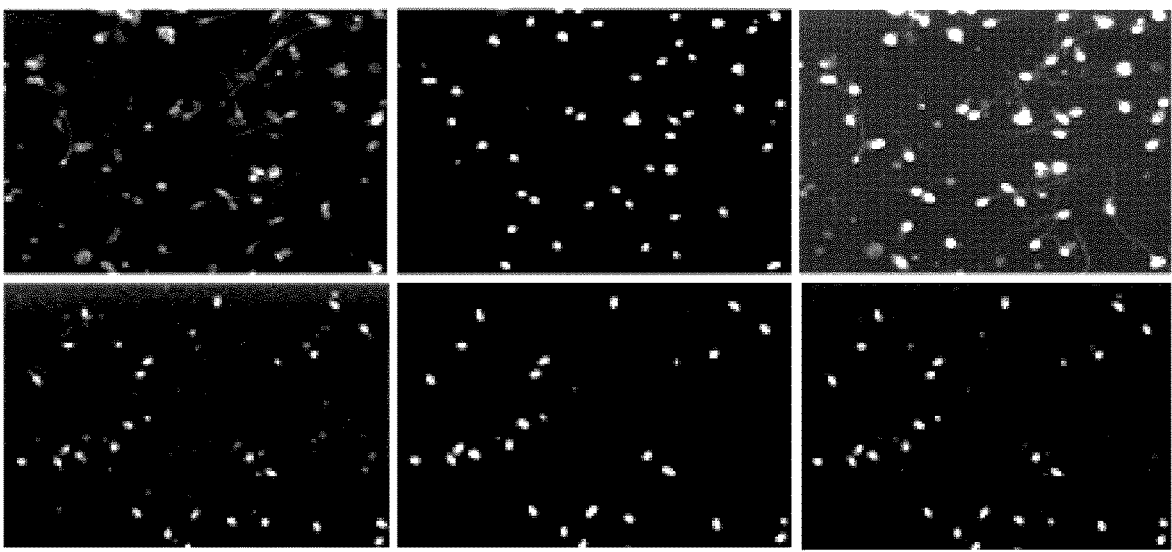
In FIG. 1B: Immunofluorescence of an ejaculate from a patient with oligo-astheno-teratozoospermia (OAT) syndrome. Vim3 distribution is predominantly detectable in the head region (upper left). Results were comparable to the distribution of Vimentin full length (V9) (lower row).
Figure 2A:
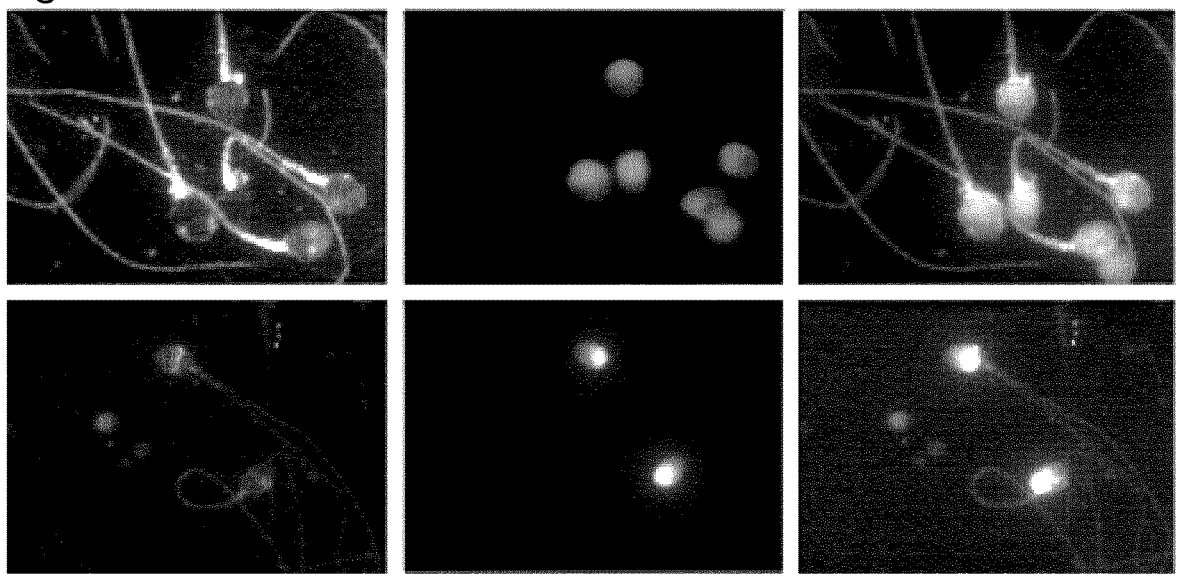
FIG. 2A: Immunofluorescence showing expression of Vim3 (upper left image) in normozoospermia. The staining of the sperm head (DAPI stain) is depicted in the images in the middle (upper middle and lower middle. Localization of the Vim3 predominantly located in the neck and tail region. The Vimentin full length (V9) (lower left) shows a dominant location in the head region.
Figure 2B:
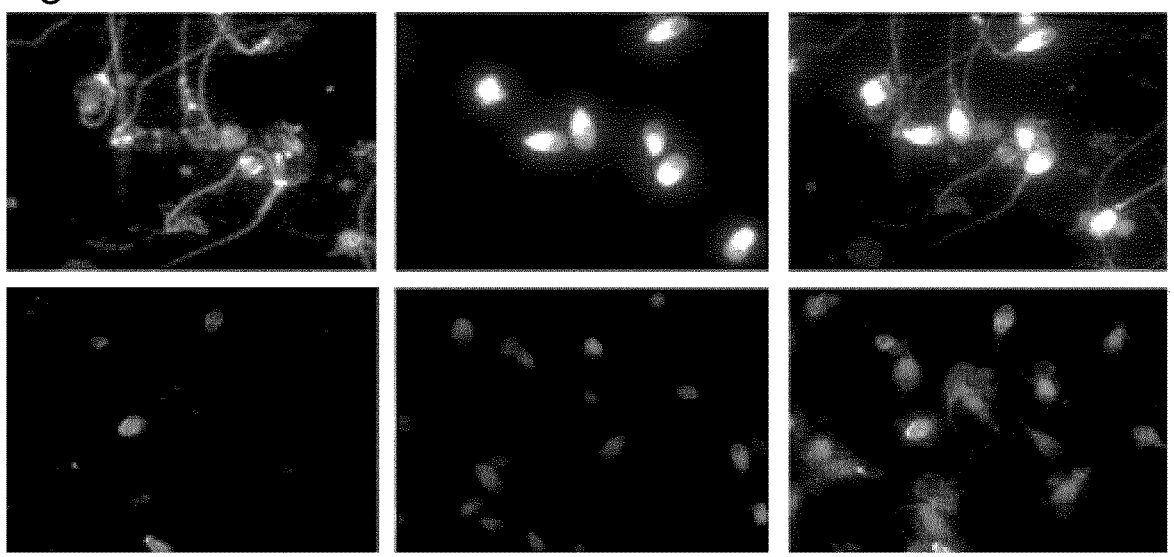
In FIG. 2B: Immunofluorescence of an ejaculate from a patient with oligo-astheno-teratozoospermia (OAT) syndrome. Vim3 distribution is predominantly detectable in the head and tail region, whereas the distribution of the full length variant is similar to the distribution in ejaculates from normozoospermia patients.
Figure 2C:
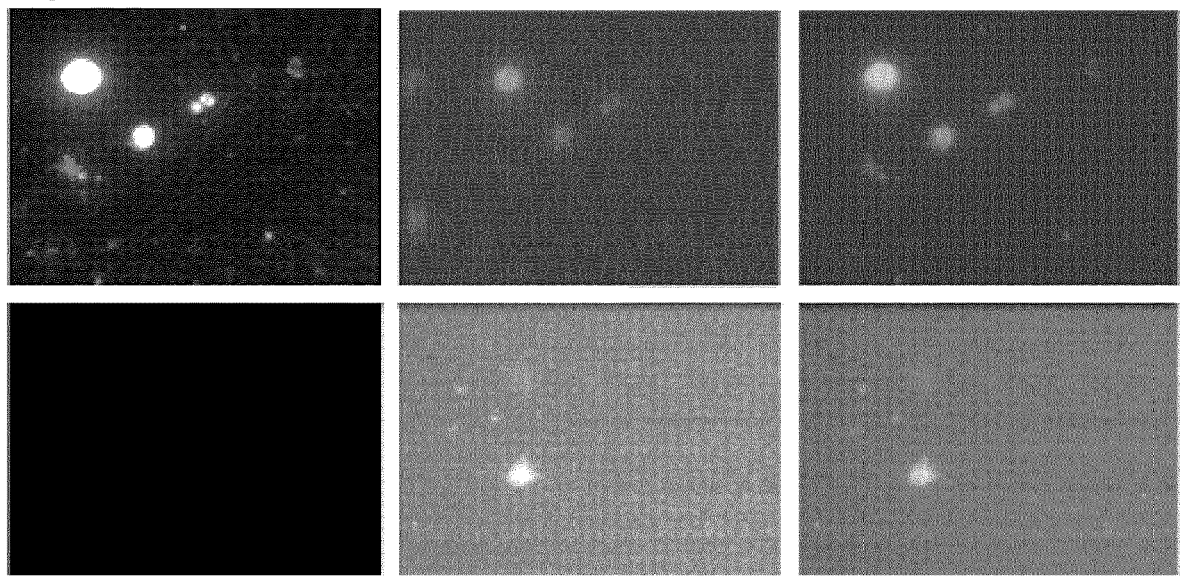
FIG. 2C: in ejaculates from azoospermia patients, no Vimentin full length was detectable at all (lower row). Vim3 expression was detectable in DNA positive cell fragments (DAPI staining).

In patients with normozoospermia Vim3 distribution was predominantly identified in the neck and tail part of sperms, whereas the distribution of the Vimentin full length (V9) shows a dominant location in the head region of the sperms especially the equatorial segment (FIGS. 1A and 2A). Comparing this immunofluorescence staining with the results from patients with OAT syndrome, a different distribution of the Vim3 variant is detectable. In case of the OAT syndrome (FIGS. 1B and 2B) the Vim3 is predominantly expressed in the head domain and to a lesser extend in the neck and tail domain. FIG. 2C shows an ejaculate sample from a patient with azoospermia. As it can be seen in the lower row, a staining with the V9 antibody did not show any signaling, however, staining the sample with the Vim3 antibody a positive signal was detectable in cells with DNA content, which was indicated by the DAPI staining.

Figure 3:
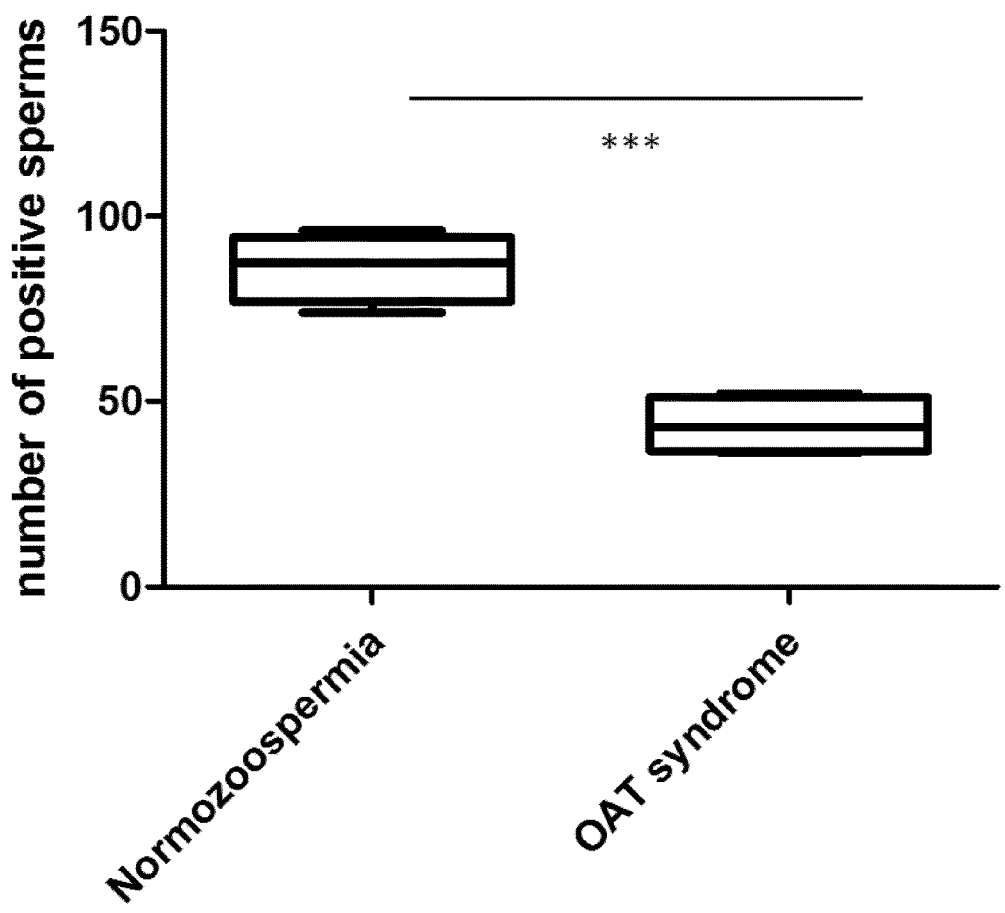
FIG. 3 shows the comparison between sperm cells from a control sample (normozoospermia) and a patient suffering from oligo-astheno-teratozoospermia (OAT) syndrome.

For calculation of the differences between patients with normozoospermia and OAT syndrome from each group 5 samples were coated on a slide, stained with Vim3 and DAPI and 100 sperms were counted. For the fluorescence intensity the normozoospermia signal of sperms was chosen as highest signal. FIG. 3 shows the statistical significant results between the normozoospermia and the OAT syndrome ($p<0.001$).

Figure 4A:
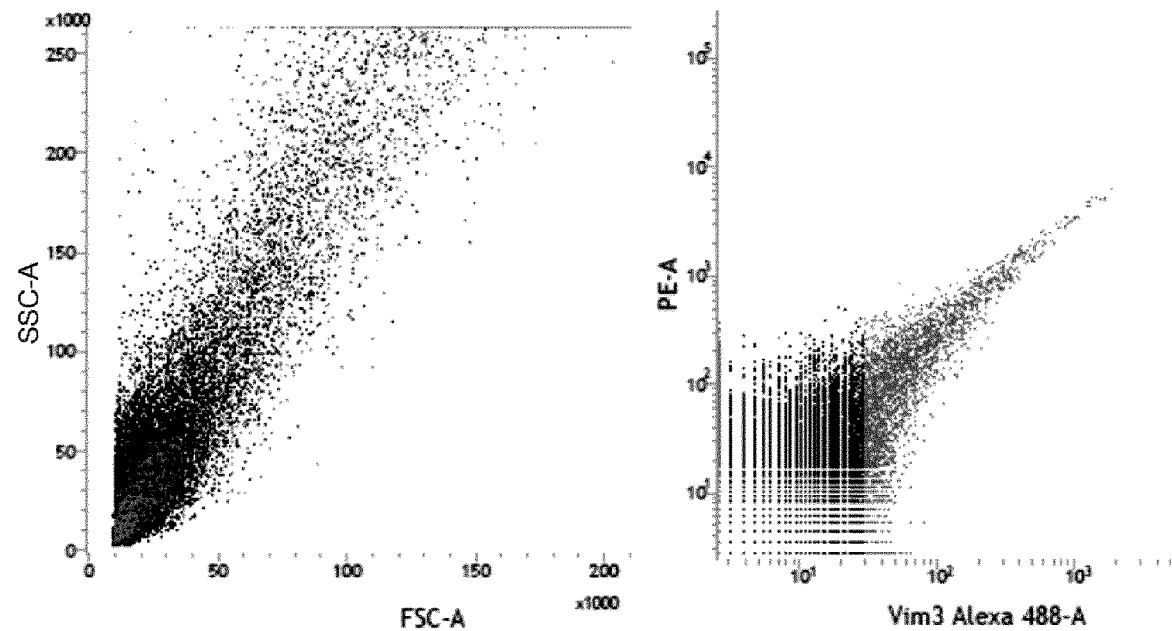
FIG. 4 shows a flow cytometry analysis of samples from patients with normozoospermia (a), OAT syndrome (b) and azoospermia (c) (FIG. 4B). Normozoospermia 60-70% of all cells were positive (n=5), OAT syndrome 10-20% positivity (n=6) and azoospermia 30-40% positivity of cells (n=4).
Figure 4B:
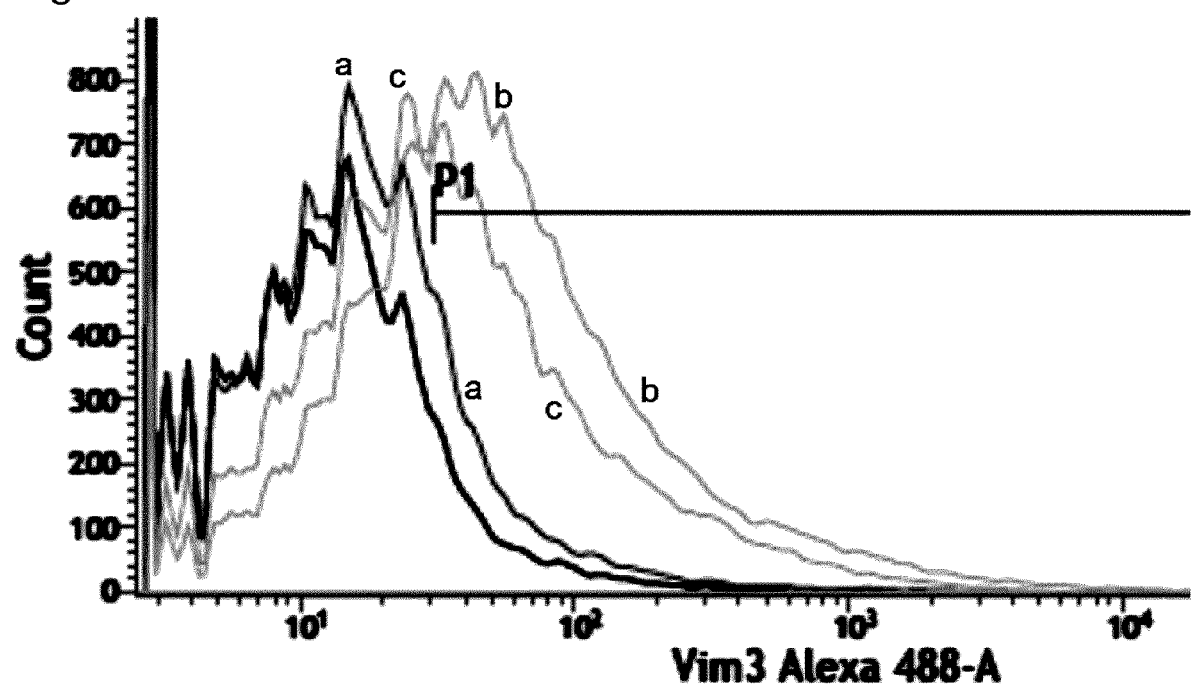
Figure 5:
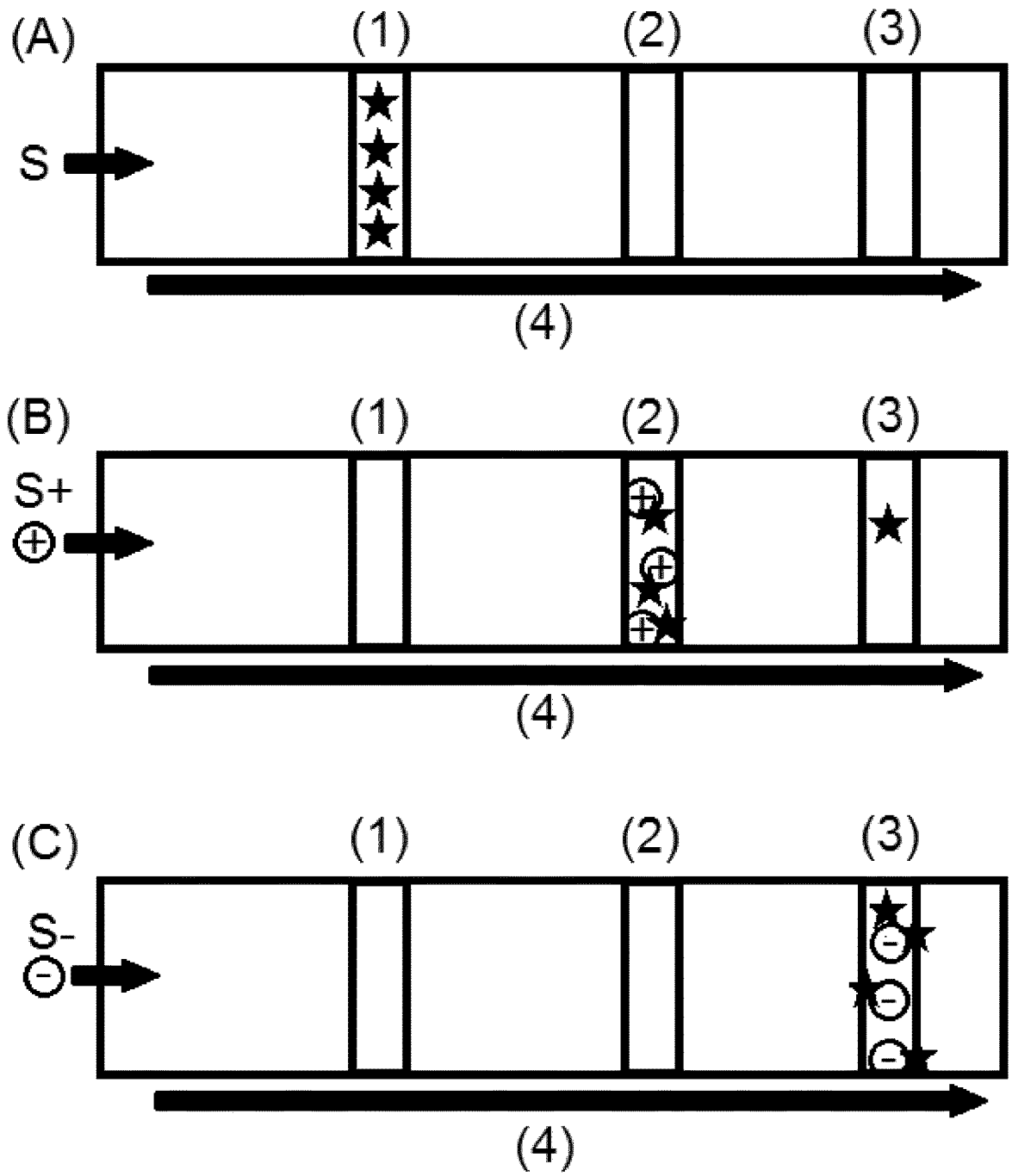
FIG. 5 shows an exemplary setup of a dipstick usable for the method of the present invention.
Figure 6:
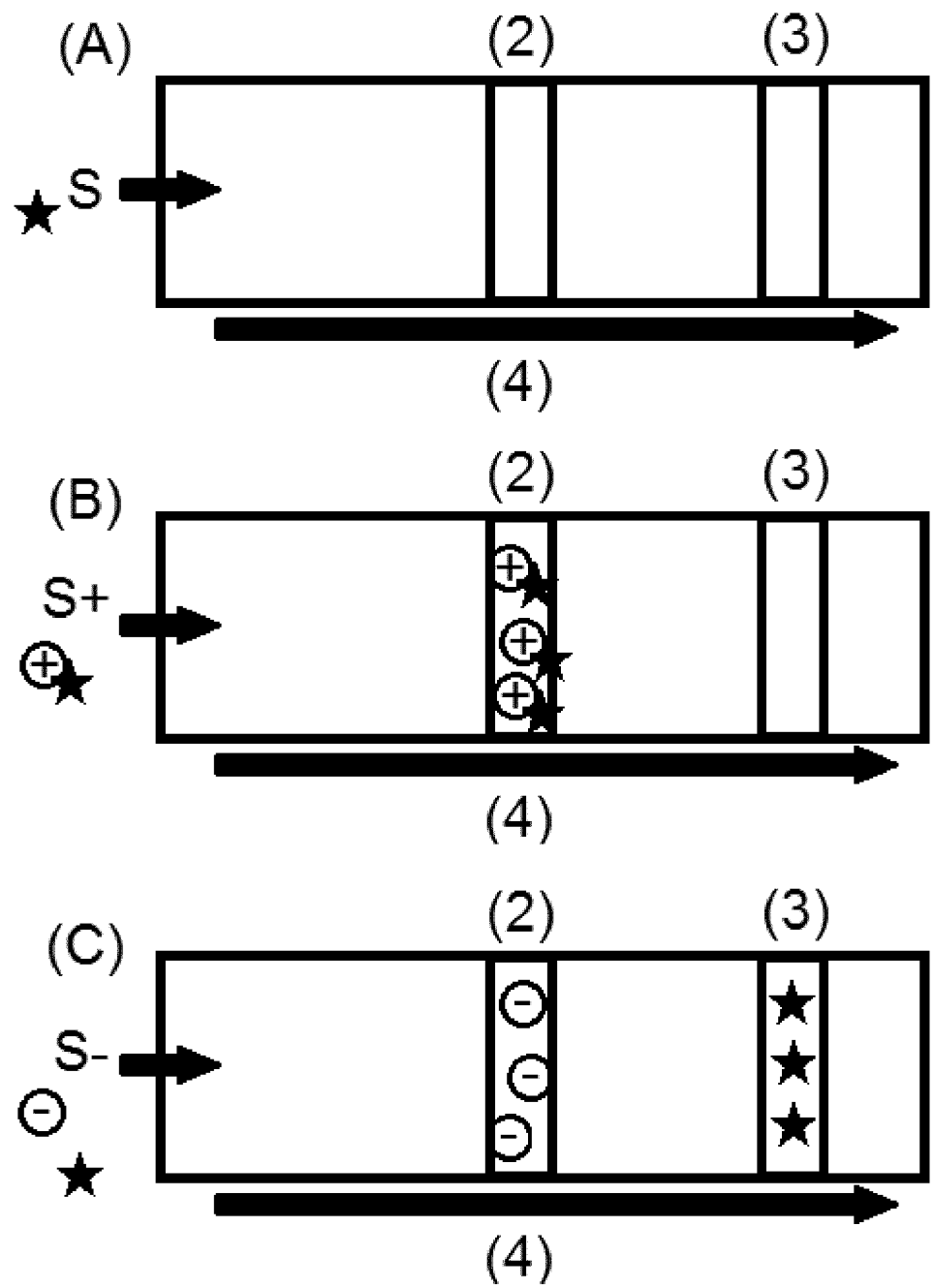
FIG. 6 shows another setup of a dipstick usable for the method of the present invention as an alternative to the one shown in FIG. 5.

Flow cytometry analysis, shown in FIG. 4, of samples from patients with normozoospermia, OAT syndrome and azoospermia, show significant differences regarding the amount of positive counted cells (FIG. 4B). Normozoospermia 60-70% of all cells were positive (n=5), OAT syndrome 10-20% positivity (n=5) and azoospermia 30-40% positivity of cells (n=5). This is depicted in the following Table 1.

TABLE 1

Statistics of the flow cytometry analysis of samples from patients with normozoospermia (Normo), OAT syndrome (OAT) and azoospermia (AZOO)

| name | events | parent = total [%] | FSC-A [mean] | SSC-A [mean] |
| --- | --- | --- | --- | --- |
| Normo:P1 | 3.581 | 7.16 | 111.565 | 159.694 |
| Normo_1:P1 | 30.433 | 60.87 | 35.320 | 53.167 |
| OAT_1:P1 | 6.796 | 13.59 | 50.037 | 68.001 |
| AZOO_1:P1 | 21.185 | 42.37 | 61.081 | 78.032 |

DISCUSSION

Beyond the classical visual microscopic analysis of ejaculates from special trained stuff, which is frequently related with enormous pressure problems for patient, a reliable marker for the presence of "healthy and mortal" sperms do not exist.

The newly identified Vim3 protein shows reliable results for the differentiation between normozoospermia and OAT syndrome, even in case of frozen samples. Meaning that the patient does, not longer, has the time pressure to provide the sample in the time permitted. Since this protein can also in "old" ejaculate samples (more or less death sperms) clearly differentiate between a "healthy" ejaculate and an ejaculate with abnormal sperms. The whole procedure for the clear identification of fertile sperms is reduced to a maximum of 2 hours with the new identified marker and flow cytometry analysis. In particular with a dipstick, far shorter analysis times are obtainable, even in the range of (few) minutes or even shorter than a minute. Also flow cytometry provides rather fast analysis. These reduce the patient psychological problems, ease the situation and shorten the period of being unknown. Being childlessness is a frequent reason for marital difficulties. The time between the first suspicion and diagnose can be unbearable long and a lot of relationships will be disturbed do the fact of being childlessness. The period of restriction is also of lower effect since the marker detects a structural protein, which is either highly expressed or low. In case of a low expression of the Vim3 protein, the sperms do have morphological changes like it is frequently the case in the OAT syndrome.

Vimentin full length cannot be used as sufficient differentiation marker, shown in FIGS. 1 and 2. Vim3 has however been identified as a surprisingly beneficial marker for fertility.

Comparison Between Teratozoospermia and Normozoospermia

Figure 7:
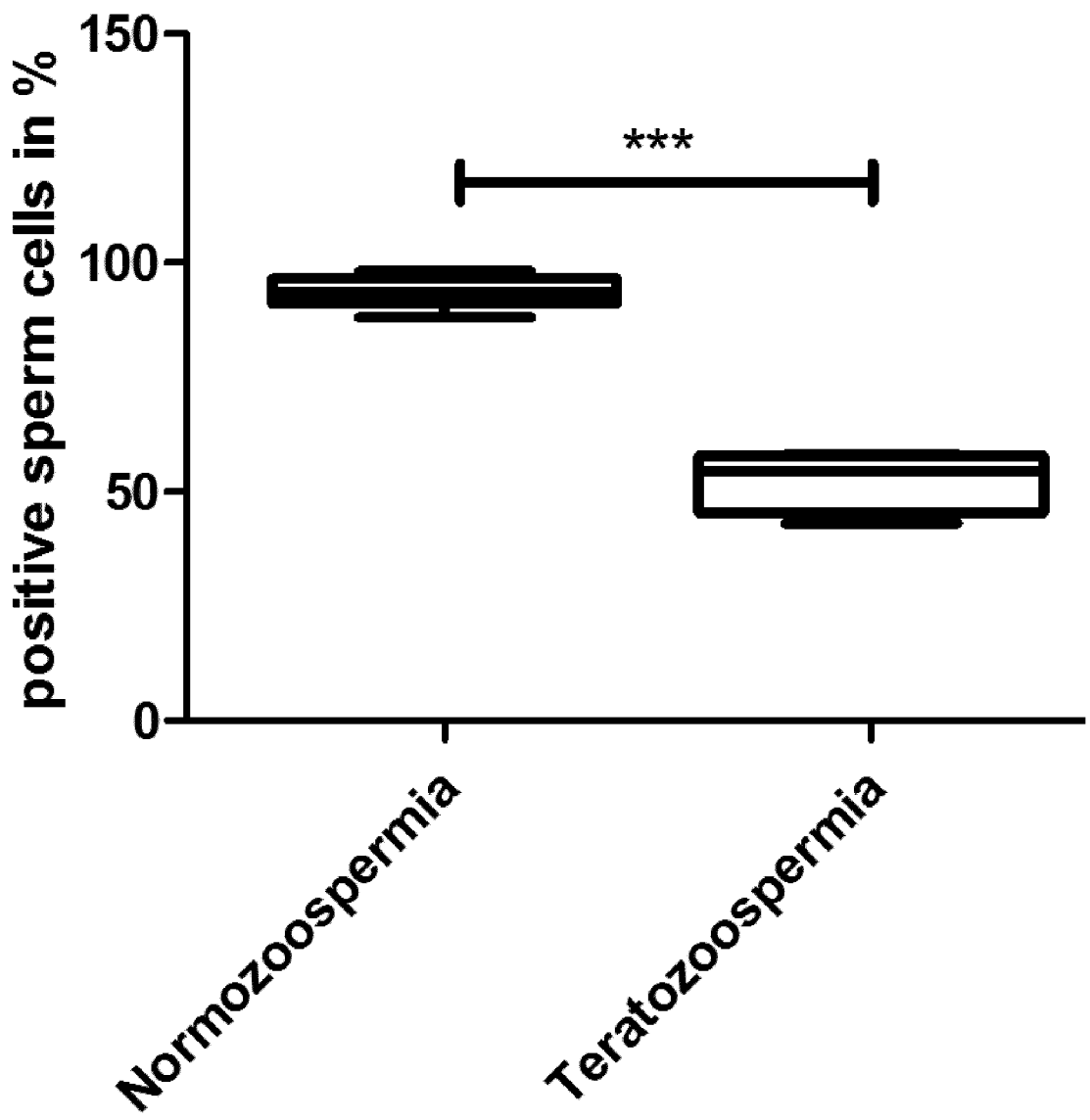
FIG. 7 shows the comparison between sperm cells from a control sample (normozoospermia) and a patient suffering from teratozoospermia. The fluorescence was at the same intensity for both. The normozoospermia was used as "standard" intensity. Four different samples of teratozoospermia were calculated and always 100 sperms were counted. The result is statistical significant and shows a pattern comparable with that found for oligo-astheno-teratozoospermia (OAT) syndrome (see FIG. 3).

Four Teratozoospermia samples were used for the analysis. 100 µl of the sperm samples from patients with teratozoospermia were used, the samples were centrifuged and washed twice with PBS. The semen was resuspended in 20 µl PBS and 10 µl were used for seminal smears on object slides. The slides were air dried and incubated for 1 hour at room temperature with the Vim3 antibody, after that the slides were washed twice in PBS and incubated for 1 hour at room temperature with a FITC labelled secondary antibody in the dark. Finally the slides were washed again in PBS and covered with DAPI mounting medium. From each sample 100 sperms were counted and compared with samples from normozoospermia patients. The same signal reduction was detectable was it was the case for the OAT syndrome, concluding, that only in sperms from normozoospermia patients the Vim3 expression is "normal" and in the teratozoospermia, as well as in the OAT syndrome, the Vim3 expression was significantly decreased and the distribution of the Vim3 signal was different and not predominately located in the neck and tail region. The results are depicted in FIG. 7. In summary, in teratozoospermia the same staining pattern was detectable as it was the case for the OAT syndrome.

Colocalization of Vim3 and Mitochondria

The same staining procedure as mentioned above was performed, followed by a special staining of the mitochondria with a Mitotracker Kit according to the manufactures protocol (Thermofisher). Furthermore, the head and the tail domain of sperms form patients with OAT, teratozoospermia and normozoospermia were cut off by means of Laser-based microdissection and separated from each other. 3D images were generated just from the neck domain. With this method it was possible to show the direct distribution of Vim3 and the mitochondria as well as the different expression of the full length version of Vimentin and the mitochondria. The degree of colocalization was determined by means of fluorescence microscopy.

Interestingly, the staining showed homologue areas, leading to the conclusion that Vim3 and mitochondria are colocalized, presumably combined, with each other. This led to the conclusion that Vim3 is present in combination with mitochondria. It was found that the signal intensity was higher in samples from patients with normozoospermia in comparison to patients with OAT or teratozoospermia. Furthermore, it was found that the colocalization of Vim3 and mitochondria was more distinct in in samples from patients with normozoospermia in comparison to patients with OAT or teratozoospermia.

The invention claimed is:

1. A method of treating a human or non-human male-female reproductive pair in which the male has low fertility comprising:
 subjecting a female human or non-human animal in said human or non-human male-female reproductive pair to artificial insemination or in vitro fertilization; and/or
 subjecting a male human or non-human animal in said human or non-human male-female reproductive pair to an effective treatment to increase fertility,
wherein the male was determined to have low fertility comprising a method of detecting total content of Vimentin variant 3 (Vim3) per spermatozoon or spatial localization of Vim3 within spermatozoa in a sperm sample S obtained from the male, wherein one or more of the following conditions are met:
 total content of Vim3 per spermatozoon was decreased compared to a fertile control;
 total content of Vim3 per spermatozoon was not higher than that of an infertile control;
 Vim3 accumulation in the mid pieces of the spermatozoa was decreased compared to a fertile control; or
 Vim3 accumulation in the mid piece of the spermatozoa was not higher than an infertile control.

2. The method of claim 1, wherein the low fertility of the male is associated with at least one pathologic condition of the donor of the spermatozoa contained in the sample S.

3. The method of claim 2, wherein the at least one pathologic condition is selected from the group consisting of oligozoospermia, asthenozoospermia and teratozoospermia.

4. The method of claim 1, wherein the steps of detecting the total content of the Vim3 per spermatozoon or the spatial localization of the Vim3 within the spermatozoa and comparing the total content or spatial localization to a fertile or infertile control are performed by a computer.

5. The method of claim 1, wherein said method of detecting the spatial localization of the Vim3 within the spermatozoa comprises the following steps:
 (i) providing an aliquot of the sample S, containing spermatozoa;
 (ii) staining intracellular Vim3 of the spermatozoa with a fluorescently labeled marker;
 (iii) detecting the spatial localization of the Vim3 within the stained spermatozoa of step (ii) by fluorescence microscopy;
 (iv) determining the degree of Vim3 accumulation in the mid piece of the spermatozoa; and
 (v) comparing the degree of Vim3 accumulation determined in step (iv) between the sample S and
  (a) at least one control sample C+ of spermatozoa of high fertility of the same species, and/or
  (b) at least one control sample C− of spermatozoa of low fertility of the same species,
wherein a decreased amount of Vim3 accumulation in the mid piece of the spermatozoa in the sample S as determined in step (v) indicates decreased fertility of the spermatozoa contained in the sample S.

6. The method of claim 5, said method further comprising the additional step of:
 (vi) comparing microscopic movability and/or morphology of the spermatozoa between the sample S and
  (a) at least one control sample C+ of spermatozoa of high fertility of the same species, and/or
  (b) at least one control sample C− of spermatozoa of low fertility of the same species, wherein a decreased amount of movability of the spermatozoa and/or a deviation in morphology of the spermatozoa in the sample S compared to C+, as determined in the step (vi), in combination with a decreased amount of Vim3 accumulation the mid pieces of the spermatozoa and/or a decreased amount of the total content of Vim3 per spermatozoon in the sample S compared to C+ as determined in step (iv), indicates decreased fertility of the spermatozoa contained in the sample S.

7. The method of claim 1, wherein the sample S is, or is derived from, an ejaculate of the male human or male non-human animal.

8. The method of claim 1, wherein the sample S is for artificial insemination.

9. The method of claim 1, wherein at least one of the following conditions are met:
 i) an amount of the total content of Vim3 per spermatozoon contained in the sample S decreased by at least 20% in comparison to the fertile control;
 ii) an amount of the total content of Vim3 per spermatozoon contained in the sample S that is not at least 10% higher than in the infertile control;
 iii) an amount of accumulation of Vim3 in the mid piece of the spermatozoa contained in the sample S decreased by at least 20% in comparison to the fertile control; and
 iv) an amount of accumulation of Vim3 in the mid piece of the spermatozoa contained in the sample S that is not at least 10% higher than in the infertile control,
indicates decreased fertility of the spermatozoa contained in the sample S.

10. The method of claim 1, wherein said method of detecting the spatial localization of the Vim3 within the spermatozoa further comprises staining Vim3 in the spermatozoa contained in the sample S prior to detecting its spatial localization.

11. The method of claim 10, wherein a Vim3-specific antibody or antibody fragment is used for staining Vim3.

12. The method of claim 10, wherein staining Vim3 comprises:
    direct immunodetection comprising providing at least one Vim3-specific labeled antibody or antibody fragment, AB1-L,
    enabling the binding of said AB1-L to the Vim3 in the spermatozoa; or
    indirect immunodetection comprising providing at least one Vim3-specific unlabeled antibody or antibody fragment, AB1-ul, and at least one labeled antibody or antibody fragment, AB2-L, specifically binding to AB1-ul,
    enabling the binding of AB1-ul to the Vim3 in the spermatozoa, and enabling the binding of AB2-L to AB1-ul.

13. The method of claim 10, further comprising fixation of the spermatozoa contained in the sample S prior to staining Vim3 in the spermatozoa.

14. The method of claim 10, wherein a fluorescently labeled marker is used for staining Vim3.

15. The method of claim 10, wherein a fluorescently labeled marker is used for staining Vim3, wherein step (ii) is detecting:
    (A) the spatial localization of the Vim3 conducted by fluorescence microscopy; and/or
    (B) the total content of the Vim3 per spermatozoon conducted by flow cytometry.

16. The method of claim 1, wherein said spermatozoa are contacted with detectably labeled marker that specifically binds to Vim3.

17. The method of claim 1, wherein total content of Vim3 per spermatozoon and/or degree of Vim3 accumulation in the mid piece is detected by microscopy, mass spectrometry, or immunochemically.

18. The method of claim 1, wherein degree of Vim3 accumulation in the mid piece is detected immunochemically.

19. The method of claim 1, wherein total content of Vim3 per spermatozoon is detected by microscopy, mass spectrometry, or immunochemically.

20. The method of claim 1, wherein detecting the total content of the Vim3 per spermatozoon or the spatial localization of the Vim3 within the spermatozoa is conducted by a microscope, a dipstick, a mass spectrometer, a flow cytometer, an ELISA, or a Western Blot.

21. The method of claim 1, wherein the method is a method of treating a human or non-human male-female couple and comprises subjecting a female human or non-human animal in said human or non-human male-female couple or reproductive pair to artificial insemination or in vitro fertilization.

22. A method for artificial insemination of a female human or non-human animal for sexual reproduction, said method comprising the following steps:
    (1) providing one or more samples S containing spermatozoa potentially suitable for sexual reproduction;
    (2) determining the fertility of the sample S of step (1) by detecting total content of the Vim3 per spermatozoon or spatial localization of the Vim3 within the spermatozoa and comparing the determined total content or spatial localization to a fertile control or an infertile control;
    (3) classifying the fertility of the sample S determined by step (2) as:
        (A) a sample S+ containing spermatozoa of high fertility, or
        (B) a sample S− containing spermatozoa of low fertility,
        by setting a threshold value between (a) a first control sample C+ of spermatozoa of high fertility and (b) a second control sample C− of spermatozoa of low fertility, wherein C+ and C− are of the same species as sample S; and
    (4) selecting and obtaining a sample S+ containing spermatozoa of higher fertility above the threshold fertility according to step (3) as sperm portion A sufficient for sexual reproduction of a human or a non-human animal containing spermatozoa of high fertility; and
    (5) conducting artificial insemination with the sperm portion A for sexual reproduction of a human or a non-human animal.

23. The method of claim 22, wherein detecting the total content of the Vim3 per spermatozoon or the spatial localization of the Vim3 within the spermatozoa is conducted by a microscope, a dipstick, a mass spectrometer, a flow cytometer, an ELISA, or a Western Blot.

24. A method for obtaining a non-human animal, said method comprising the steps:
    (I) providing a variety of samples S containing spermatozoa potentially suitable for sexual reproduction;
    (II) determining the fertility of the samples S of step (I) by detecting total content of the Vim3 per spermatozoon or spatial localization of the Vim3 within the spermatozoa and comparing the determined total content or spatial localization to a fertile control or an infertile control;
    (III) identifying a sample S+ of high fertility suitable for sexual reproduction based on the findings of step (II);
    (IV) inseminating a non-human female animal of species SP susceptible for pregnancy with the selected sample S+ as identified in step (III) by artificial insemination or copulation with the male non-human animal from which sample S+ has been derived from; and
    (V) enabling the gestation of progeny obtained from step (IV) in the female animal, subsequent birth and obtaining the non-human animal.

25. The method of claim 24, wherein the non-human animal is a non-human male animal bearing spermatozoa of high fertility.

* * * * *